(12) United States Patent
Messing et al.

(10) Patent No.: US 7,365,050 B2
(45) Date of Patent: Apr. 29, 2008

(54) METHODS FOR MODULATING A DRUG-RELATED EFFECT OR BEHAVIOR

(75) Inventors: Robert O. Messing, Foster City, CA (US); Philip M. Newton, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 105 days.

(21) Appl. No.: 10/913,697

(22) Filed: Aug. 5, 2004

(65) Prior Publication Data

US 2005/0054574 A1 Mar. 10, 2005

Related U.S. Application Data

(60) Provisional application No. 60/493,960, filed on Aug. 8, 2003.

(51) Int. Cl.
*A61K 38/00* (2006.01)
*G01N 33/53* (2006.01)

(52) U.S. Cl. ............................................. 514/2; 435/7.1
(58) Field of Classification Search ................ 530/350; 514/12; 435/7.1
See application file for complete search history.

(56) References Cited

U.S. PATENT DOCUMENTS

| | | | |
|---|---|---|---|
| 5,859,186 A * | 1/1999 | Justice et al. | 530/324 |
| 6,011,035 A | 1/2000 | Snutch et al. | |
| 6,057,332 A * | 5/2000 | Michne et al. | 514/272 |
| 6,267,945 B1 | 7/2001 | Zamponi | |
| 6,310,059 B1 | 10/2001 | Snutch | |
| 6,353,091 B1 | 3/2002 | Lipscombe et al. | |
| 6,387,897 B1 | 5/2002 | Snutch | |
| 6,492,375 B2 | 12/2002 | Snutch | |
| 6,617,322 B2 | 9/2003 | Snutch | |
| 2004/0034035 A1 | 2/2004 | Snutch et al. | |
| 2004/0044004 A1 | 3/2004 | Snutch et al. | |

FOREIGN PATENT DOCUMENTS

WO WO 2005/015159 A3 2/2005

OTHER PUBLICATIONS

McMahon et al., PKC ε mediates up-regulation of N-type calcium channels by ethanol, 2000, Mol. Pharmacol. vol. 57, pp. 53-58.*
Litten et al., Medications for alcohol, illicit drug, and tobacco dependence. An update of research findings, J. Subst Abuse Treat. Mar. 1999, vol. 16, No. 2, pp. 105-112. Review.*
Allgaier C. (2002) Ethanol sensitivity of NMDA receptors. Neurochem Int 41:377-382.
Beuckmann CT, Sinton CM, Miyamoto N, Ino M, Yanagisawa M (2003) N-type calcium channel alpha1B subunit ($Ca_v2.2$) knock-out mice display hyperactivity and vigilance state differences. J Neurosci 23:6793-6797.
Bowers BJ, Owen EH, Collins AC, Abeliovich A, Tonegawa S, Wehner JM (1999) Decreased ethanol sensitivity and tolerance development in gamma-protein kinase C null mutant mice is dependent on genetic background. Alcoholism, Clinical and Experimental Research 23:387-397.
Brooks SP, Hennebry G, McAlpin GP, Norman G, Little HJ (2002) Nimodipine prevents the effects of ethanol in tests of memory. Neuropharmacology 42:577-585.
Chester JA, Lumeng L, Li TK, Grahame NJ (2003) High- and low-alcohol-preferring mice show differences in conditioned taste aversion to alcohol. Alcohol Clin Exp Res 27:12-18.
Davies M. (2003) The role of GABAA receptors in mediating the effects of alcohol in the central nervous system. J Psychiatry Neurosci 28:263-274.
De A, Boyadjieva NI, Sarkar DK (1999) Effect of voltage-dependent calcium channel blockers on ethanol-induced beta-endorphin release from hypothalamic neurons in primary cultures. Alcohol Clin Exp Res 23:850-855.
De Beun R, Schneider R, Klein A, Lohmann A, De Vry J (1996) Effects of nimodipine and other calcium channel antagonists in alcohol-preferring AA rats. Alcohol 13:263-271.
Dudek BC, Phillips TJ (1990) Distinctions among sedative, disinhibitory, and ataxic properties of ethanol in inbred and selectively bred mice. Psychopharmacology (Berl) 101:93-99.
Dunlap K, Luebke JI, Turner TJ (1995) Exocytotic Ca2+ channels in mammalian central neurons. Trends in Neurosciences 18:89-98.
Fadda F, Garau B, Colombo G, Gessa GL (1992) Isradipine and other calcium channel antagonists attenuate ethanol consumption in ethanol-preferring rats. Alcoholism: Clinical and Experimental Research 16:449-452.
Gruner W. and Silva L. R. (1994) Omega-conotoxin sensitivity and presynaptic inhibition of glutamatergic sensory neurotransmission in vitro. J Neurosci 14:2800-2808.
Hjelmstad G. O. and Fields H. L. (2003) Kappa opioid receptor activation in the nucleus accumbens inhibits glutamate and GABA release through different mechanisms. J Neurophysiol 89:2389-2395.

(Continued)

*Primary Examiner*—Robert B. Mondesi
(74) *Attorney, Agent, or Firm*—Jones Day

(57) ABSTRACT

The present invention provides a method of reducing or preventing a drug-related effect or behavior in a subject by inhibiting N-type calcium channels. In addition, the invention provides a variety of prescreening and screening methods aimed at identifying agents that modulate a drug-related effect or behavior. These methods involve assaying test agent binding to N-type calcium channels or channel subunits. Alternatively, test agents can be screened for their ability to alter the level of N-type calcium channels, channel subunit polypeptide or RNA, or the depolarization-induced inward calcium current mediated by these channels. Finally, the invention also provides a diagnostic method that entails measuring one or more of these levels and determining risk for a drug-related effect or behavior based on comparison to the corresponding level for a control population.

14 Claims, 7 Drawing Sheets

OTHER PUBLICATIONS

Hodge CW, Mehmert KK, Kelley SP, McMahon T, Haywood A, Olive MF, Wang D, Sanchez-Perez AM, Messing RO (1999) Supersensitivity to allosteric GABAA receptor modulators and alcohol in mice lacking PKCε. Nature Neuroscience 2:997-1002.

Kim C, Jun K, Lee T, Kim SS, McEnery MW, Chin H, Kim HL, Park JM, Kim DK, Jung SJ, Kim J, Shin HS (2001) Altered nociceptive response in mice deficient in the alpha(1B) subunit of the voltage-dependent calcium channel. Mol Cell Neurosci 18:235-245.

Kitamura G., Ohta T., Kai T., Kon Y. and Ito S. (2002) Inhibitory effects of opioids on voltage-dependent Ca(2+) channels and catecholamine secretion in cultured porcine adrenal chromaffin cells. Brain Res 942:11-22.

Krystal J. H., Petrakis I. L., Mason G., Trevisan L. and D'Souza D. C. (2003) N-methyl-D-aspartate glutamate receptors and alcoholism: reward, dependence, treatment, and vulnerability. Pharmacol Ther 99:79-94.

Kuzmin A, Semenova S, Zvartau E, De Vry J (1999) Effects of calcium channel blockade on intravenous self-administration of ethanol in rats. Eur Neuropsychopharmacol 9:197-203.

Little HJ (1995) The role of calcium channels in drug dependence. Drug Alcohol Depend 38:173-194.

Mackie and Hille (1992) Cannabinoids inhibit N-type calcium channels in neuroblastoma-glioma cells. Proc. Natl. Acad. Sci., USA 89:3825-29.

McMahon T, Anderson R, Metten P, Crabbe JC, Messing RO (2000) Protein kinase C epsilon mediates up-regulation of N-type calcium channels by ethanol. Molecular Pharmacology 57:53-58.

Momiyama T. and Koga E. (2001) Dopamine D(2)-like receptors selectively block N-type Ca(2+) channels to reduce GABA release onto rat striatal cholinergic interneurones. J Physiol 533:479-492.

Naassila M, Ledent C, Daoust M (2002) Low ethanol sensitivity and increased ethanol consumption in mice lacking adenosine A2A receptors. J Neurosci 22:10487-10493.

Naassila M, Pierrefiche O, Ledent C, Daoust M (2004) Decreased alcohol self-administration and increased alcohol sensitivity and withdrawal in CB1 receptor knockout mice. Neuropharmacology 46:243-253.

Oswald L. M. and Wand G. S. (2004) Opioids and alcoholism. Physiol Behav 81:339-358.

Phillips T. J., Brown K. J., Burkhart-Kasch S., Wenger C. D., Kelly M. A., Rubinstein M., et al. (1998) Alcohol preference and sensitivity are markedly reduced in mice lacking dopamine D2 receptors. Nat Neurosci 1:610-615.

Pucilowski O, Ayensu WK, D'Ercole AJ (1996) Insulin-like growth factor I expression alters acute sensitivity and tolerance to ethanol in transgenic mice. Eur J Pharmacol 305:57-62.

Rezvani AH, Grady DR, Janowsky DS (1991) Effect of calcium-channel blockers on alcohol consumption in alcohol-drinking monkeys. Alcohol & Alcoholism 26:161-167.

Rezvani AH, Janowsky DS (1990) Decreased alcohol consumption by verapamil in alcohol preferring rats. Progress in Neuro-Psychopharmacology and Biological Psychiatry 14:623-631.

Risinger FO, Boyce JM (2002) Conditioning tastant and the acquisition of conditioned taste avoidance to drugs of abuse in DBA/2J mice. Psychopharmacology (Berl) 160:225-232.

Roberts A. J., McDonald J. S., Heyser C. J., Kieffer B. L., Matthes H. W., Koob G. F., et al. (2000) mu-Opioid receptor knockout mice do not self-administer alcohol. J Pharmacol Exp Ther 293:1002-1008.

Ruiz-Velasco and Ikeda (2000) Multiple G-Protein βγ Combinations Produce Voltage-Dependent Inhibition of N-Type Calcium Channels in Rat Superior Cervical Ganglion Neurons. J. Neuroscience 20:2183-91.

Soldo BL, Moises HC (1997) μ-opioid receptor activation decreases N-type Ca2+ current in magnocellular neurons of the rat basal forebrain. Brain Research 758:118-126.

Solem M, McMahon T, Messing RO (1997) Protein kinase A regulates inhibition of N- and P/Q-type calcium channels by ethanol in PC12 cells. Journal of Pharmacology and Experimental Therapeutics 282:1487-1495.

Spanagel R, Siegmund S, Cowen M, Schroff KC, Schumann G, Fiserova M, Sillaber I, Wellek S, Singer M, Putzke J (2002) The neuronal nitric oxide synthase gene is critically involved in neurobehavioral effects of alcohol. J Neurosci 22:8676-8683.

Thiele TE, Koh MT, Pedrazzini T (2002) Voluntary alcohol consumption is controlled via the neuropeptide Y Y1 receptor. J Neurosci 22:RC208.

Thiele TE, Marsh DJ, Ste. Marie L, Bernstein IL, Palmiter RD (1998) Ethanol consumption and resistance are inversely related to neuropeptide Y levels. Nature 396:366-369.

Thiele TE, Willis B, Stadler J, Reynolds JG, Bernstein IL, McKnight GS (2000) High ethanol consumption and low sensitivity to ethanol-induced sedation in protein kinase A-mutant mice. Journal of Neuroscience 20:RC75.

Twitchell W., Brown S. and Mackie K. (1997) Cannabinoids inhibit N- and P/Q-type calcium channels in cultured rat hippocampal neurons. J Neurophysiol 78:43-50.

Tzschentke TM (1998) Measuring reward with the conditioned place preference paradigm: a comprehensive review of drug effects, recent progress and new issues. Prog Neurobiol 56:613-672.

Wand G, Levine M, Zweifel L, Schwindinger W, Abel T (2001) The cAMP-protein kinase A signal transduction pathway modulates ethanol consumption and sedative effects of ethanol. Journal of Neuroscience 21:5297-5303.

Watson WP, Little HJ (1999) Correlation between increases in dihydropyridine binding in vivo and behavioural signs of ethanol withdrawal in mice. Alcohol Alcohol 34:35-42.

Weinshenker D, Rust NC, Miller NS, Palmiter RD (2000) Ethanol-associated behaviors of mice lacking norepinephrine. Journal of Neuroscience 20:3157-3164.

McDonough et al., "Interactions among Toxins That Inhibit N-type and P-type Calcium Channels," J. Gen. Physiol, Apr. 2002, vol. 17, No. 4, pp. 313-328.

* cited by examiner

METHODS FOR MODULATING A DRUG-RELATED EFFECT OR BEHAVIOR

CROSS-REFERENCE TO RELATED APPLICATIONS

This application claims the benefit of U.S. Provisional Application No. 60/493,960, filed Aug. 8, 2003, which is hereby incorporated by reference in its entirety.

STATEMENT AS TO RIGHTS TO INVENTIONS MADE UNDER FEDERALLY SPONSORED RESEARCH AND DEVELOPMENT

This invention was made with government support under grant no. AA08117 and AA013588. The Government may have certain rights in the invention.

FIELD OF THE INVENTION

This invention relates to methods of reducing a drug-related effect or behavior, such as those associated with ethanol, cannabinoids, and opioids, as well as related screening and diagnostic methods.

BACKGROUND OF THE INVENTION

Voltage-gated calcium channels mediate calcium entry into neurons and regulate firing patterns, neurotransmitter release, gene expression, and differentiation. They have been classified as L-, N-, P/Q-, R and T-type according to their electrophysiological and pharmacological properties (Dunlap et al., 1995). There has been extensive research into the role of L-type calcium channels in mediating the behavioral effects of ethanol, driven largely by the widespread availability of high affinity antagonists for these channels (Little, 1995). For example, the dihydropyridine nimodipine inhibits both the acquisition and expression of ethanol self-administration (De Beun et al., 1996; Kuzmin et al., 1999) and prevents the inhibitory effects of ethanol on memory in radial arm maze and object recognition tests (Brooks et al., 2002). L-type channel antagonists also reduce alcohol withdrawal seizures in rodents (Watson and Little, 1999).

N-type calcium channels are multimeric complexes containing at least three kinds of subunits. Two of these, β and $α_2δ$ are also found in all neuronal voltage-gated calcium channels. The third kind of subunit, α1 is unique for each type of calcium channel, and $Ca_v2.2$ $α_1$, is unique for the N-type calcium channel.

Ethanol has been shown to increase the level of N-type calcium channels by a protein kinase Cε (PKCε)-mediated mechanism. McMahon et al. (2000) Mol. Pharm. 57:53-58. Brief exposure to ethanol (Solem et al. (1997) J. Pharmacol. Exp. Ther. 282:1487-95), opiates (Soldo and Moises (1997) Brain Res. 758:118-126), or cannabinoids (Mackie and Hille (1992) Proc. Natl. Acad. Sci., USA 89:3825-29) inhibits N-type channels.

Despite the cellular and molecular data indicating that ethanol modulates N-type calcium channels, it was not known whether this interaction contributed to the behavioral effects of ethanol. This question was addressed using a genetic approach, i.e., by studying ethanol responses in mice that carry a null mutation in the calcium channel subunit $Ca_v2.2$ and, therefore, lack functional N-type calcium channels (Kim et al., 2001). $Ca_v2.2$ null mice develop normally with no overt phenotypic abnormalities. In dorsal root ganglion cultures from $Ca_v2.2$ null mice, the level of L-, P/Q- and R-type calcium channel currents are unchanged compared to wild-type neurons, indicating a selective absence of N-type channel activity that does not alter the function of remaining voltage-gated calcium channels (Kim et al., 2001).

SUMMARY OF THE INVENTION

Mice lacking N-type calcium channels showed decreased ethanol conditioned place preference and taste aversion, reduced ethanol consumption, and altered ataxic and hypnotic responses to acute ethanol administration. These findings indicate an important role for N-type channels in the reinforcing and rewarding properties of ethanol and other drugs.

Accordingly, the invention provides a method of reducing or preventing a drug-related effect or behavior by inhibiting an N-type calcium channel in a subject. The method is generally directed toward effects or behaviors associated with drugs of abuse, such as, for example, ethanol, cannabinoids, and opioids. Examples of drug-related effects or behavior that the method can address include sedative effects, hypnotic effects, drug reward, and drug consumption.

In preferred embodiments, the method entails administering an N-type calcium channel inhibitor to the subject. Examples of non-selective N-type calcium channel inhibitors useful in the method include omega conotoxin MVIIC, omega grammotoxin SIA, and omega agatoxin IIIA. Preferred N-type calcium channel inhibitors are selective inhibitors, such as omega-conotoxin MvIIA, omega conotoxin GVIA, omega conotoxin CNVIIA, omega conotoxin CVID (AM336), Ptu1, NMED-126, and NMED-160.

In one embodiment, the N-type calcium channel inhibitor inhibits a function of N-type calcium channels. In a variation of this embodiment, the N-type calcium channel inhibitor inhibits phosphorylation of N-type calcium channels. In another variation of this embodiment, the N-type calcium channel inhibitor enhances the interaction between N-type calcium channels and β-γ subunits of a G protein.

The N-type calcium channel inhibitor can also reduce the level of N-type calcium channels in a tissue. In a variation of this embodiment, the N-type calcium channel inhibitor reduces the level of N-type $Ca_v2.2$ subunits in the tissue.

The invention also provides prescreening and screening methods, which are preferably carried out in vitro. In one embodiment, a method of prescreening for an agent that modulates a drug-related effect or behavior entails:

a) contacting a test agent with an N-type calcium channel or a subunit thereof; and b) determining whether the test agent specifically binds to the N-type calcium channel or subunit; and c) if the test agent specifically binds to the N-type calcium channel or subunit, selecting the test agent as a potential modulator of a drug-related effect or behavior. In a variation of this embodiment, the test agent is contacted with the N-type $Ca_v2.2$ subunit.

In another embodiment, a method of prescreening for an agent that modulates a drug-related effect or behavior entails:

a) contacting a test agent with polypeptide comprising, or a polynucleotide encoding, an N-type $Ca_v2.2$ subunit; and b) determining whether the test agent specifically binds to the polypeptide comprising, or a polynucleotide encoding, an N-type $Ca_v2.2$ subunit; and c) if the test agent specifically binds to the polypeptide comprising, or a polynucleotide encoding, an N-type Ca$_v$2.2 subunit, selecting the test agent as a potential modulator of a drug-related effect or behavior.

A screening method of the invention entails:
a) contacting a test agent with a cell that expresses an N-type calcium channel in the absence of test agent, or a fraction of said cell; and
b) after contact with the test agent, determining the level of:
   (i) N-type calcium channels;
   (ii) N-type Ca$_v$2.2 subunit polypeptide;
   (iii) N-type Ca$_v$2.2 subunit RNA; or
   (iv) depolarization-induced inward calcium current;
c) if the level of (b) is altered, selecting the test agent as a potential modulator of a drug-related effect or behavior. In a variation of this embodiment, the test agent is contacted with the cell or cellular fraction in the presence of a drug, such as ethanol, a cannabinoid, and/or an opioid. In preferred embodiments, a test agent that reduces the particular level is selected. A test agent selected in this screening method can be tested for in vivo effects by measuring the ability of the selected test agent to modulate a drug-related effect or behavior in an animal model.

In another embodiment, a screening method of the invention entails:
a) selecting an N-type calcium channel modulator as a test agent; and
b) measuring the ability of the selected test agent to modulate a drug-related effect or behavior in an animal model. In preferred variations of this embodiment, an N-type calcium channel inhibitor is selected as the test agent. The drug can be a drug of abuse, such as ethanol, a cannabinoid, and an opioid. The method is useful for examining the effect of test agents on effects or behaviors such as, for example, sedative effects, hypnotic effects, ataxic effects, drug reward, and drug consumption.

Any test agent selected in any of the prescreening or screening methods of the invention can be recorded in a database of agents that may modulate a drug-related effect or behavior. The selected test agent can also be combined with a pharmaceutically acceptable carrier.

The invention additionally provides a diagnostic method for assessing a subject's risk for experiencing a drug-related effect or developing a drug-related behavior. This method entails:
determining the level of:
   (i) N-type calcium channels;
   (ii) N-type Ca$_v$2.2 subunit polypeptide;
   (iii) N-type Ca$_v$2.2 subunit RNA; or
   (iv) depolarization-induced inward calcium current;
in a biological sample from the subject,
wherein risk for experiencing a drug-related effect or developing a drug-related behavior is directly correlated with said level. This determination can be followed by administration of an N-type calcium channel inhibitor to a subject determined to have a high risk for experiencing a drug-related effect or developing a drug-related behavior.

The invention also provides kits useful for carrying out the methods of the invention. One kit of the invention includes an N-type calcium channel inhibitor in a pharmaceutically acceptable carrier and instructions for carrying out a method of reducing a drug-related effect or behavior. Another kit of the invention is a diagnostic kit including:
a) a component that specifically binds to:
   (i) N-type calcium channels;
   (ii) N-type Ca$_v$2.2 subunit polypeptide;
   (iii) N-type Ca$_v$2.2 subunit RNA; and
b) instructions for carrying out a method of assessing risk of drug-related effects or behaviors.

BRIEF DESCRIPTION OF THE DRAWINGS

FIG. 1A shows ethanol consumption (grams/kg/day) plotted versus ethanol concentration (percent volume/volume). Ca$_v$2.2 null mice consumed a lower amount of ethanol at all doses except the highest. Two-way ANOVA with a between-subjects factor for genotype and a within-subjects factor for ethanol concentration showed an effect of genotype (F[1,136]=5.35, P=0.027), and ethanol concentration (F[4,136]=7.33, P<0.001). *P<0.05 compared with null mice at same concentration of ethanol (Tukey test).

FIG. 1B shows ethanol preference, calculated by dividing volume of ethanol consumed (ml/day) by total volume of fluid consumed (ml/day) and multiplying by 100%, plotted versus ethanol concentration. Ca$_v$2.2 null mice exhibited a lower preference for ethanol at all doses except the highest. Two-way ANOVA with a between-subjects factor for genotype and a within-subjects factor for ethanol concentration showed an effect of genotype (F[1.136]=4.23, P=0.047), and ethanol concentration (F[4,136]=43.20, P<0.001). *P<0.05 compared with null mice at same concentration of ethanol (Tukey test).

FIG. 1C shows water consumption (grams/kg/day) plotted versus ethanol concentration. There was no difference in water consumption between the genotypes (F [1,136]=0.35, p=0.56).

FIG. 1D shows variations of this study in which bitter (quinine) or sweet (saccharin) solutions were substituted for the ethanol solution. Consumption of these solutions (ml/kg body weight) is shown for 2 different concentrations of each solution. No significant differences were seen between the Ca$_v$2.2 null mice and the wild-type littermates (P>0.05, two-tailed unpaired t-tests).

FIG. 3A shows the LORR duration (minutes) for each group of mice. Mice were given an intraperitoneal injection of ethanol (3.6 g/kg using 20% v/v ethanol in 0.9% w/v saline) and tested for the loss of the righting reflex. $Ca_v2.2$ null mice (n=12) exhibited a shorter LORR duration than wild-type littermates (n=11). $P<0.05$ (two-tailed t-test).

FIG. 3B shows the blood alcohol level upon recovery from the LORR (mg/dl) for each group of mice. $Ca_v2.2$ null mice (n=12) regained the righting reflex at a higher blood alcohol level than wild-type mice (n=11). $P<0.05$ (two-tailed t-test).

FIG. 3C shows that the threshold dose of ethanol (10% ethanol in 0.9% v/v saline) required to induce loss of righting reflex is significantly higher in $Ca_v2.2$ null mice (values are mean+/−95% confidence interval). n=6 for both genotypes.

FIG. 3D shows the blood alcohol level at 30 min intervals during the course of the study, demonstrating that ethanol clearance was similar in both genotypes after intraperitoneal injection of 4 g/kg ethanol. n=6 for both genotypes.

FIGS. 4A and B. Mice were trained to remain on a constant-velocity (20 rpm) rotarod for 180 sec and then administered 1.5 g/kg (A) or 2 g/kg (B) ethanol by intraperitoneal injection and tested every 15 min for their ability to stay on the rotarod. Two-way ANOVA with a between-subjects factor for genotype and repeated measure for time showed a main effect of time (F[4,72]=4.73, P=0.002), but not of genotype, and there was no significant interaction between genotype and time.

FIG. 4C. Mice were trained to remain on an accelerating (4-40 rpm) rotarod for 300s. On a subsequent day, they were trained once further, and then given an intraperitoneal injection of ethanol (2 gram/kg) and tested every 15 min for their ability to stay on the rotarod. Mice lacking $Ca_v2.2$ (open circles) were more sensitive than wild-type littermates (closed circles) to the ataxic effects of ethanol. Two-way ANOVA with a between-subjects factor for genotype and a repeated measure for time showed an effect of genotype (F[1,68]=8.32, P<0.01) and time (F[4,68]=10.594, P<0.001), with an interaction between genotype and time (F[4,68]=4.25, P=0.004). *P<0.05 compared with null mice at the same time (Tukey test).

FIG. 5A shows the mean HIC score (see Example 5) plotted versus time after removal from the vapor chambers (hours). $Ca_v2.2$ null mice generally had higher HIC scores throughout the withdrawal period than wild-type littermates. Two-way repeated measures ANOVA showed effects of genotype (F [1,144]=7.88, P=0.013) and time (F [9,144] =10.27, P<0.0001) with an interaction between these factors, F [9,144]=2.82, P=0.004). *P<0.05 compared with wild-type mice at the same timepoint (Tukey test).

FIG. 5B shows the area under the HIC curve shown in FIG. 5A. *P<0.05, two-tailed t-test.

FIG. 5C shows that blood alcohol levels did not differ between the genotypes after ethanol vapor exposure.

FIG. 7A indicates that $Ca_v2.2$ null mice showed a significantly shorter LORR duration than +/+littermates (*P<0.05 by two-tailed t-test).

DETAILED DESCRIPTION

Figure 1:
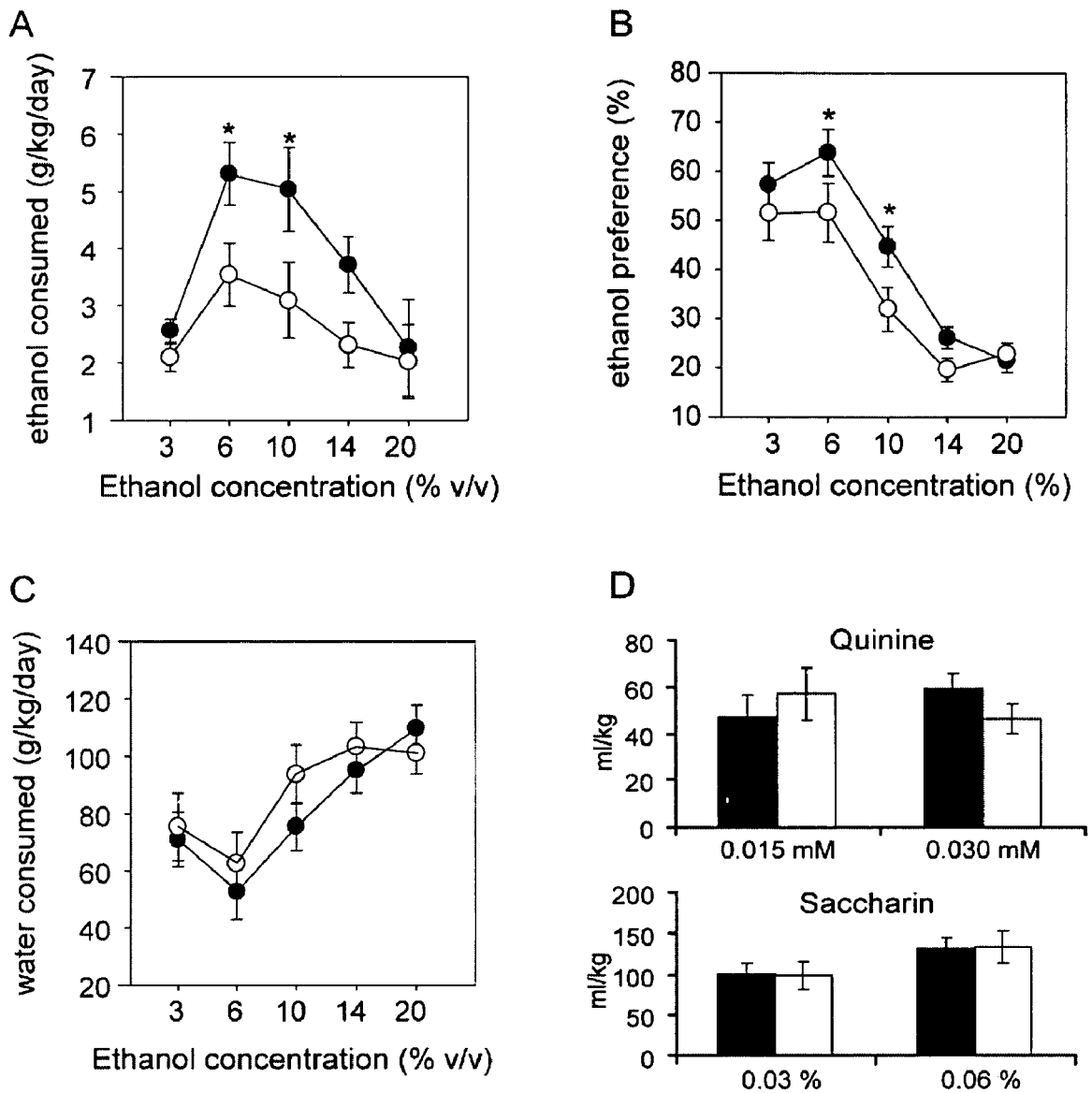
FIG. 1A-D shows the results of a study of voluntary ethanol consumption and preference using transgenic knockout mice that are null for the N-type calcium channel Ca$_v$2.2 subunit and their wild-type littermates. See Example 1. In a two-bottle choice paradigm, mice were allowed free access to water and an ethanol solution and consumption of each was monitored every two days. The ethanol concentration was increased every fourth day. Open circles or bars indicate the results for Ca$_v$2.2 null mice; closed circles or bars indicate the results for wild-type mice. n=15 Ca$_v$2.2 null and 21 wild-type mice in A-C, and 12 Ca$_v$2.2 null and 12 wild-type mice in D.

The present invention relates to the discovery that N-type calcium channels modulate certain drug-related effects and behaviors. The role of N-type calcium channels in these effects and behaviors has been demonstrated, for the first time, in vivo using knockout mice that are null for the $Ca_v2.2$ subunit, which is unique to the N-type channel. Thus, these knockout mice cannot produce functional N-type calcium channels. The results obtained from the studies of these mice described herein indicate that certain drug-related effects and behaviors can be reduced or prevented by inhibiting these channels. In addition, these studies have given rise to various screening methods based on assaying test agents for their ability to bind to N-type calcium channels or channel subunits or to alter an N-type calcium channel-related parameter. Furthermore, the $Ca_v2.2$ null knockout studies have lead to the development of a diagnostic method for assessing a subject's risk for drug-related effects or behaviors. These methods are of particular interest with respect to drugs of abuse, such as ethanol, cannabinoids, and opioids.

Definitions

Terms used in the claims and specification are defined as set forth below unless otherwise specified.

The term "receptor" refers to a molecule or complex of molecules, typically (although not necessarily) a protein(s), that is specifically bound by one or more particular ligands. The receptor is said to be a receptor for such ligand(s). Ligand-receptor binding, in many instances, induces one or more biological responses.

A "G protein-coupled receptor" is a receptor that interacts with a "G protein" upon ligand-receptor binding.

The term "G protein" refers to any heterotrimeric protein that binds GDP. Ligand-receptor binding stimulates a receptor-G protein interaction that results in the exchange GDP bound to the G protein for GTP. G proteins are made up of $\alpha$, $\beta$, and $\gamma$ subunits. One or more G protein subunits then typically interact with one or more effectors or effector systems that mediate a biological response.

The term "channel" refers to a structure that forms a pore in a cell membrane through which ions pass under particular conditions. A "calcium channel" is a channel through which $Ca^{2+}$ ions pass. An "N-type calcium channel" is a voltage-gated calcium channel, wherein membrane depolarization leads to an inward calcium current. N-type calcium channels include an N-type $Ca_v2.2$ subunit and are inhibited by G protein $\beta$-$\gamma$ subunits.

The following terms encompass polypeptides that are identified in Genbank by the following designations, as well as polypeptides that are at least about 70% identical to polypeptides identified in Genbank by these designations: subunits of N-type calcium channels, particularly N-type $Ca_v2.2$. In alternative embodiments, these terms encompass polypeptides identified in Genbank by these designations and polypeptides sharing at least about 80, 90, 95, 96, 97, 98, or 99% identity.

A "modulator of an N-type calcium channel" is either an inhibitor or an enhancer of an N-type calcium channel.

A "non-selective" modulator of an N-type calcium channel is an agent that modulates other calcium channels at the concentrations typically employed for N-type channel modulation.

A "selective" modulator of an N-type calcium channel significantly modulates one or more of the normal functions of an N-type calcium channel at a concentration at which other calcium channels are not significantly modulated.

A modulator "acts directly on an N-type calcium channel" when the modulator binds to the N-type channel.

A modulator "acts indirectly on an N-type calcium channel" when the modulator binds to a molecule other than the N-type channel, which binding results in modulation of the N-type channel.

An "inhibitor of an N-type calcium channel" is an agent that reduces, by any mechanism, the extent of depolarization-induced inward calcium current through N-type calcium channels, as compared to that observed in the absence (or presence of a smaller amount) of the agent. An inhibitor of an N-type calcium channel can affect: (1) the expression; mRNA stability; or protein trafficking, modification (e.g., phosphorylation), or degradation of an N-type calcium channel or one or more of its subunits (e.g., N-type $Ca_v2.2$), or (2) one or more of the normal functions of an N-type calcium channel, such the depolarization-induced inward calcium current. An inhibitor of an N-type calcium channel can be non-selective or selective.

An "enhancer of an N-type calcium channel" is an agent that increases, by any mechanism, the extent of depolarization-induced inward calcium current through N-type calcium channels, as compared to that observed in the absence (or presence of a smaller amount) of the agent. An enhancer of an N-type calcium channel can affect: (1) the expression; mRNA stability; or protein trafficking, modification (e.g., phosphorylation), or degradation of an N-type calcium channel or one or more of its subunits (e.g., N-type $Ca_v2.2$), or (2) one or more of the normal functions of an N-type calcium channel, such the depolarization-induced inward calcium current. An enhancer of an N-type calcium channel can be non-selective or selective.

The terms "polypeptide" and "protein" are used interchangeably herein to refer a polymer of amino acids, and unless otherwise limited, include atypical amino acids that can function in a similar manner to naturally occurring amino acids.

The terms "amino acid" or "amino acid residue," include naturally occurring L-amino acids or residues, unless otherwise specifically indicated. The commonly used one- and three-letter abbreviations for amino acids are used herein (Lehninger, A. L. (1975) Biochemistry, 2d ed., pp. 71-92, Worth Publishers, N.Y.). The terms "amino acid" and "amino acid residue" include D-amino acids as well as chemically modified amino acids, such as amino acid analogs, naturally occurring amino acids that are not usually incorporated into proteins, and chemically synthesized compounds having the characteristic properties of amino acids (collectively, "atypical" amino acids). For example, analogs or mimetics of phenylalanine or proline, which allow the same conformational restriction of the peptide compounds as natural Phe or Pro are included within the definition of "amino acid."

Exemplary atypical amino acids, include, for example, those described in International Publication No. WO 90/01940 as well as 2-amino adipic acid (Aad) which can be substituted for Glu and Asp; 2-aminopimelic acid (Apm), for Glu and Asp; 2-aminobutyric acid (Abu), for Met, Leu, and other aliphatic amino acids; 2-aminoheptanoic acid (Ahe), for Met, Leu, and other aliphatic amino acids; 2-aminoisobutyric acid (Aib), for Gly; cyclohexylalanine (Cha), for Val, Leu, and Ile; homoarginine (Har), for Arg and Lys; 2,3-diaminopropionic acid (Dpr), for Lys, Arg, and His; N-ethylglycine (EtGly) for Gly, Pro, and Ala; N-ethylasparagine (EtAsn), for Asn and Gln; hydroxyllysine (Hyl), for Lys; allohydroxyllysine (Ahyl), for Lys; 3- (and 4-) hydoxyproline (3Hyp, 4Hyp), for Pro, Ser, and Thr; allo-isoleucine (Aile), for Ile, Leu, and Val; amidinophenylalanine, for Ala; N-methylglycine (MeGly, sarcosine), for Gly, Pro, and Ala; N-methylisoleucine (MeIle), for Ile; norvaline (Nva), for Met and other aliphatic amino acids; norleucine (Nle), for Met and other aliphatic amino acids; ornithine (Orn), for Lys, Arg, and His; citrulline (Cit) and methionine sulfoxide (MSO) for Thr, Asn, and Gln; N-methylphenylalanine (MePhe), trimethylphenylalanine, halo (F, Cl, Br, and I) phenylalanine, and trifluorylphenylalanine, for Phe.

The terms "identical" or "percent identity," in the context of two or more amino acid or nucleotide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) J. Mol. Biol. 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Natl. Acad. Sci. USA, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

A "radioligand binding assay" is an assay in which a biological sample (e.g., cell, cell lysate, tissue, etc.) containing a receptor is contacted with a radioactively labeled ligand for the receptor under conditions suitable for specific binding between the receptor and ligand, unbound ligand is removed, and receptor binding is determined by detecting bound radioactivity.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated, F light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778).

The phrases "an effective amount" and "an amount sufficient to" refer to amounts of a biologically active agent that produce an intended biological activity.

The term "polynucleotide" refers to a deoxyribonucleotide or ribonucleotide polymer, and unless otherwise limited, includes known analogs of natural nucleotides that can function in a similar manner to naturally occurring nucleotides. The term "polynucleotide" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "polynucleotide" encompasses double-stranded nucleic acid molecules, as well as single-stranded molecules. In double-stranded polynucleotides, the polynucleotide strands need not be coextensive (i.e., a double-stranded polynucleotide need not be double-stranded along the entire length of both strands).

As used herein, the term "complementary" refers to the capacity for precise pairing between two nucleotides. I.e., if a nucleotide at a given position of a nucleic acid molecule is capable of hydrogen bonding with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions.

The phrase "stringent hybridization conditions" generally refers to a temperature about 5° C. lower than the melting temperature ($T_m$) for a specific sequence at a defined ionic strength and pH. Exemplary stringent conditions suitable for achieving specific hybridization of most sequences are a temperature of at least about 60° C. and a salt concentration of about 0.2 molar at pH7.

"Specific hybridization" refers to the binding of a nucleic acid molecule to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

The phrase "a drug-related effect or behavior" refers to an in vivo effect or behavior that occurs in response to a drug. Exemplary effects include stimulant, sedative, hypnotic, and ataxic effects, as well as drug reward. An example of a drug-related behavior is drug consumption.

A "sedative effect" refers to a decrease in activity and/or excitement in a subject.

A "hypnotic effect" includes an increase in drowsiness and/or a facilitation of the onset and/or maintenance of sleep.

An "ataxic effect" refers to a decrease in motor coordination.

The term "drug reward" refers to the tendency of a drug to induce a subject to alter their behavior to obtain more of the drug.

"Drug consumption" refers to the amount of drug consumed by a subject over a selected period of time.

"Drug preference" refers to a subject's preference for the drug over a comparable substance that lacks particular effects of the drug.

A "test agent" is any agent that can be screened in the prescreening or screening assays of the invention. The test agent can be any suitable composition, including a small molecule, peptide, or polypeptide.

An agent is said to "modulate" a drug-related effect or behavior if the agent inhibits or enhances the drug-related effect or behavior.

The term "therapy," as used herein, encompasses the treatment of an existing condition as well as preventative treatment (i.e., prophylaxis). Accordingly, "therapeutic" effects and applications include prophylactic effects and applications, respectively.

A used herein, the term "high risk" refers to an elevated risk as compared to that of an appropriate matched (e.g., for age, sex, etc.) control population.

Method of Reducing a Drug-Related Effect or Behavior

A. In General

The invention provides a method of reducing or preventing a drug-related effect or behavior. The method entails inhibiting an N-type calcium channel in a subject, whereby the drug-related effect or behavior is reduced or prevented. Generally, the method is carried out by administering an N-type calcium channel inhibitor to a subject. The method is useful for addressing undesirable effects or behaviors associated with a variety of drugs, particularly sedative-hypnotic and analgesic drugs. In particular embodiments, the method is used to reduce or prevent effects or behaviors associated with drugs such as ethanol, cannabinioids, opioids, and the like. Exemplary cannabinioids include Tetrahydrocannabinol (THC), dronabinol, arachidonylethanolamide (anandamide, AEA). Exemplary opioids include morphine, codeine, heroin, butorphanol, hydrocodone, hydromorphone, levorphanol, meperidine, nalbuphine, oxycodone, fentanyl, methadone, propoxyphene, remifentanil, sufentanil, and pentazocine.

Examples of undesirable drug-related effects or behaviors that can be reduced or prevented according to the method of the invention include sedative and hypnotic effects; drug reward; and drug consumption.

The subject of the method can be any individual that has N-type calcium channels. Examples of suitable subjects include research animals, such as *Drosophila melanogaster*, mice, rats, guinea pigs, rabbits, cats, dogs, as well as monkeys and other primates, and humans. The subject can be an individual who is regularly, or intermittently, using one or more of the above drugs or an individual who is at risk for such use.

The method of the invention entails inhibiting the N-type calcium channel to a degree sufficient to reduce or prevent the drug-related effect(s) and/or behavior(s) of interest. In various embodiments, the N-type calcium channel is inhibited by at least about 10, 20, 30, 40, 50, 60, 70, 80, 90, and 95 percent, as determined by any suitable measure of channel inhibition (such as, for example, any of the assays described herein).

Any kind of N-type calcium channel inhibitor that is tolerated by the subject can be employed in the method of the invention. Thus, the inhibitor can be a polypeptide (such as, e.g., an anti-N-type calcium channel antibody), a polynucleotide (e.g., one that encodes an inhibitory polypeptide), or a small molecule. In particular embodiments, when the inhibitor is a polynucleotide, the polynucleotide is introduced into the subject's cells, where the encoded polypeptide is expressed in an amount sufficient to inhibit N-type calcium channels.

Inhibition N-type channels can be achieved by any available means, e.g., inhibition of: (1) the expression, mRNA stability, protein trafficking, modification (e.g., phosphorylation), or degradation of an N-type calcium channel or one or more of its subunits (e.g., N-type $Ca_v2.2$), or (2) one or more of the normal functions of an N-type calcium channel, such the depolarization-induced inward calcium current.

As phosphorylation of N-type calcium channels by protein kinase C (PKC) enhances N-type channel function, channel function can be inhibited by inhibiting this phosphorylation. PKCε has been implicated as the PKC isozyme that mediates channel phosphorylation. Therefore, N-type channels can be inhibited using a general PKC inhibitor or a selective PKCε inhibitor. PKC inhibitors are well-known. For instance, U.S. Pat. No. 5,783,405 describes a large number of peptides that inhibit PKC isozymes. Of these, the εV1-1, εV1-2, εV1-3, εV1-4, εV1-5 and εV1-6 peptides are selective for PKCε and are preferred peptide inhibitors. Peptide εV1-2 is a particularly preferred inhibitory peptide. Small-molecule inhibitors of PKC are described in U.S. Pat. Nos. 5,141,957, 5,204,370, 5,216,014, 5,270,310, 5,292,737, 5,344,841, 5,360,818, and 5,432,198. These molecules belong to the following classes: N,N'-Bis-(sulfonamido)-2-amino-4-iminonaphthalen-1-ones; N,N'-Bis-(amido)-2-amino-4-iminonaphthalen-1-ones; vicinal-substituted carbocyclics; 1,3-dioxane derivatives; 1,4-Bis-(aminohydroxyalkylamino)-anthraquinones; furocoumarinsulfonamides; Bis-(hydroxyalkylamino)-anthraquinones; and N-aminoalkyl amides. Due to their relative ease of administration (for instance, via transdermal delivery or ingestion), small molecule inhibitors of PKCε are, in some instances, preferred over peptide inhibitors.

In addition, interaction of N-type calcium channels with the β-γ subunits of G proteins has been shown to inhibit N-type channel function. Therefore, channel function can be inhibited by any means of enhancing Gβ-γ interaction with N-type channels. For example, activation of any of a number of G protein-coupled receptors leads to Gβ-γ inhibition of N-type calcium channels. Ruiz-Velasco and Ikeda, J. Neuroscience 20:2183-2191 (2000). Accordingly, an agonist of such a receptor can be used in the present method to inhibit N-type calcium channels.

In one embodiment, N-type calcium channel inhibition is achieved by reducing the level of N-type calcium channels in a tissue having such channels. N-type calcium channels are expressed in neurons of the central and peripheral nervous systems. Thus, the method of the invention can target N-type calcium channels in brain, dorsal root ganglion neurons, and sympathetic ganglion neurons. In a variation of this embodiment, N-type channel level is reduced by reducing the level of N-type $Ca_v2.2$ subunits in the tissue. This can be achieved using, e.g., antisense or RNA interference (RNAI) techniques to reduce the level of N-type $Ca_v2.2$ RNA available for translation.

The N-type calcium channel inhibitor can be non-selective or selective for N-type calcium channels. Examples of non-selective inhibitors suitable for use in the invention include omega conotoxin MVIIC, omega grammotoxin SIA, and omega agatoxin IIIA. Preferred embodiments employ a selective inhibitor, such as, for example, omega-conotoxin MVIIA, omega conotoxin GVIA, omega conotoxin CNVIIA (Favreau et al., 2001), omega conotoxin CVID (AM336; Lewis et al., 2000), Ptul (a toxin from the assassin bug Peirates turpis; Bernard et al. 2001), NMED-126, and NMED-160 (both of the latter two compounds are produced by NeuroMed Technologies, Inc., Vancouver, British Columbia, Calif.). Additional N-type calcium channel inhibitors useful in the invention are described in U.S. Pat. Nos. 6,617,322, 6,492,375; 6,387,897; 6,310,059; 6,267, 945; 6,011,035 and in published U.S. application Ser. No. 10/409,868 (published Mar. 4, 2004; Publication No. 20040044004) and Ser. No. 10/409,763 (published Feb. 19, 2004; Publication No. 20040034035).

B. Compositions

For research and therapeutic applications, an N-type calcium channel inhibitor is generally formulated to deliver inhibitor to a target site in an amount sufficient to inhibit N-type calcium channels at that site.

Inhibitor compositions of the invention optionally contain other components, including, for example, a storage solution, such as a suitable buffer, e.g., a physiological buffer. In a preferred embodiment, the composition is a pharmaceutical composition and the other component is a pharmaceutically acceptable carrier, such as are described in Remington's Pharmaceutical Sciences (1980) 16th editions, Osol, ed., 1980.

A pharmaceutically acceptable carrier suitable for use in the invention is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid [EDTA]), a sugar alcohol (such as mannitol and sorbitol), a salt-forming counterion (e.g., sodium), and/or an anionic surfactant (such as Tween™, Pluronics™, and PEG). In one embodiment, the pharmaceutically acceptable carrier is an aqueous pH-buffered solution.

Preferred embodiments include sustained-release pharmaceutical compositions. An exemplary sustained-release composition has a semipermeable matrix of a solid hydrophobic polymer to which the inhibitor is attached or in which the inhibitor is encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(−)-3-hydroxybutyric acid. Such matrices are in the form of shaped articles, such as films, or microcapsules.

Where the inhibitor is a polypeptide, exemplary sustained release compositions include the polypeptide attached, typically via ε-amino groups, to a polyalkylene glycol (e.g., polyethylene glycol [PEG]). Attachment of PEG to proteins is a well-known means of reducing immunogenicity and extending in vivo half-life (see, e.g., Abuchowski, J., et al. (1977) J. Biol. Chem. 252:3582-86. Any conventional "pegylation" method can be employed, provided the "pegylated" variant retains the desired function(s).

In another embodiment, a sustained-release composition includes a liposomally entrapped inhibitor. Liposomes are small vesicles composed of various types of lipids, phospholipids, and/or surfactants. These components are typically arranged in a bilayer formation, similar to the lipid arrangement of biological membranes. Liposomes containing N-type calcium channel inhibitors are prepared by known methods, such as, for example, those described in Epstein, et al. (1985) PNAS USA 82:3688-92, and Hwang, et al., (1980) PNAS USA, 77:4030-34. Ordinarily the liposomes in such preparations are of the small (about 200-800 Angstroms) unilamellar type in which the lipid content is greater than about 30 mol. percent cholesterol, the specific percentage being adjusted to provide the optimal therapy. Useful liposomes can be generated by the reverse-phase evaporation method, using a lipid composition including, for example, phosphatidylcholine, cholesterol, and PEG-derivatized phosphatidylethanolamine (PEG-PE). If desired, liposomes are extruded through filters of defined pore size to yield liposomes of a particular diameter.

Pharmaceutical compositions can also include an inhibitor adsorbed onto a membrane, such as a silastic membrane, which can be implanted, as described in International Publication No. WO 91/04014.

Pharmaceutical compositions of the invention can be stored in any standard form, including, e.g., an aqueous solution or a lyophilized cake. Such compositions are typically sterile when administered to subjects. Sterilization of an aqueous solution is readily accomplished by filtration through a sterile filtration membrane. If the composition is stored in lyophilized form, the composition can be filtered before or after lyophilization and reconstitution.

In particular embodiments, the methods of the invention employ pharmaceutical compositions containing a polynucleotide encoding a polypeptide inhibitor of N-type calcium channels. Such compositions optionally include other components, as for example, a storage solution, such as a suitable buffer, e.g., a physiological buffer. In a preferred embodiment, the composition is a pharmaceutical composition and the other component is a pharmaceutically acceptable carrier as described above.

Preferably, compositions containing polynucleotides useful in the invention also include a component that facilitates entry of the polynucleotide into a cell. Components that facilitate intracellular delivery of polynucleotides are well-known and include, for example, lipids, liposomes, water-oil emulsions, polyethylene imines and dendrimers, any of which can be used in compositions according to the invention. Lipids are among the most widely used components of this type, and any of the available lipids or lipid formulations can be employed with polynucleotides useful in the invention. Typically, cationic lipids are preferred. Preferred cationic lipids include N-[1-(2,3-dioleyloxy)propyl]-n,n,n-trimethylammonium chloride (DOTMA), dioleoyl phosphotidylethanolamine (DOPE), and/or dioleoyl phosphatidylcholine (DOPC). Polynucleotides can also be entrapped in liposomes, as described above.

In another embodiment, polynucleotides are complexed to dendrimers, which can be used to introduce polynucleotides into cells. Dendrimer polycations are three-dimensional, highly ordered oligomeric and/or polymeric compounds typically formed on a core molecule or designated initiator by reiterative reaction sequences adding the oligomers and/or polymers and providing an outer surface that is positively changed. Suitable dendrimers include, but are not limited to, "starburst" dendrimers and various dendrimer polycations. Methods for the preparation and use of dendrimers to introduce polynucleotides into cells in vivo are well known to those of skill in the art and described in detail, for example, in PCT/US83/02052 and U.S. Pat. Nos. 4,507,466; 4,558,120; 4,568,737; 4,587,329; 4,631,337; 4,694,064; 4,713,975; 4,737,550; 4,871,779; 4,857,599; and 5,661,025.

For therapeutic use, polynucleotides useful in the invention are formulated in a manner appropriate for the particular indication. U.S. Pat. No. 6,001,651 to Bennett et al. describes a number of pharmaceutical compositions and formulations suitable for use with an oligonucleotide therapeutic as well as methods of administering such oligonucleotides.

C. Administration

Methods for in vivo administration do not differ from known methods for administering small-molecule drugs or therapeutic polypeptides, peptides, or polynucleotides encoding them. Suitable routes of administration include, for example, topical, intravenous, intraperitoneal, intracerebral, intraventricular, intramuscular, intraocular, intraarterial, or intralesional routes. Pharmaceutical compositions of the invention can be administered continuously by infusion, by bolus injection, or, where the compositions are sustained-release preparations, by methods appropriate for the particular preparation.

D. Dose

The dose of inhibitor is sufficient to inhibit N-type calcium channels, preferably without significant toxicity. For therapeutic applications, the dose of inhibitor depends, for example, upon the therapeutic objectives, the route of administration, and the condition of the subject. Accordingly, it is necessary for the clinician to titer the dosage and modify the route of administration as required to obtain the optimal therapeutic effect. Generally, the clinician begins with a low dose and increases the dosage until the desired therapeutic effect is achieved. Starting doses for a given inhibitor can be extrapolated from in vitro data.

Methods of Screening for Agents that Modulate a Drug-Related Effect or Behavior

The role of N-type calcium channels in mediating drug-related effects and behaviors makes the N-type channel an attractive target for agents that modulate these effects and behaviors. Accordingly, the invention provides prescreening and screening methods aimed at identifying such agents. The prescreening/screening methods of the invention are generally, although not necessarily, carried out in vitro. Accordingly, screening assays are generally carried out, for example, using purified or partially purified components in cell lysates or fractions thereof, in cultured cells, or in a biological sample, such as a tissue or a fraction thereof.

A. Prescreening Based on Binding to N-Type Calcium Channels or a Subunit Thereof The invention provides a prescreening method based on assaying test agents for specific binding to an N-type calcium channel or a subunit thereof. Agents that specifically bind to N-type channels, or a subunit thereof, have the potential to modulate channel function, and thereby modulate one or more drug-related effects and/or behaviors.

In one embodiment, therefore, a prescreening method of the invention entails contacting a test agent with an N-type calcium channel or a subunit thereof, such as the N-type $Ca_v2.2$ subunit. Specific binding of the test agent to the N-type channel or subunit is then determined. If specific binding is detected, the test agent is selected as a potential modulator of a drug-related effect or behavior.

Such prescreening is generally most conveniently accomplished with a simple in vitro binding assay. Means of assaying for specific binding of a test agent to a polypeptide are well known to those of skill in the art. In preferred binding assays, the polypeptide is immobilized and exposed to a test agent (which can be labeled), or alternatively, the test agent(s) are immobilized and exposed to the polypeptide (which can be labeled). The immobilized species is then washed to remove any unbound material and the bound material is detected. To prescreen large numbers of test agents, high throughput assays are generally preferred. Various screening formats are discussed in greater detail below.

B. Screening Based on Binding to Polynucleotides Encoding N-type Calcium Channel Subunits The invention also provides a prescreening method based on screening test agents for specific binding to a polynucleotide encoding an N-type calcium channel subunit. Agents that specifically bind to such polynucleotides have the potential to modulate the expression of the encoded N-type calcium channel subunit, and thereby modulate one or more drug-related effects and/or behaviors.

In one embodiment, therefore, a prescreening method of the invention entails contacting a test agent with a polynucleotide encoding an N-type calcium channel subunit, such as the N-type $Ca_v2.2$ subunit. Specific binding of the test agent to the polynucleotide is then determined. If specific binding is detected, the test agent is selected as a potential modulator of a drug-related effect or behavior.

Such prescreening is generally most conveniently accomplished with a simple in vitro binding assay. Means of assaying for specific binding of a test agent to a polynucleotide are well known to those of skill in the art. In preferred binding assays, the polynucleotide is immobilized and exposed to a test agent (which can be labeled), or alternatively, the test agent(s) are immobilized and exposed to the polynucleotide (which can be labeled). The immobilized species is then washed to remove any unbound material and the bound material is detected. To prescreen large numbers of test agents, high throughput assays are generally preferred. Various screening formats are discussed in greater detail below.

C. Screening Based on Levels of N-type Calcium Channels or Channel Subunit Polypeptides or RNA Test agents, including, for example, those identified in a prescreening assay of the invention can also be screened to determine whether the test agent affects the levels of N-type calcium channels or channel subunit polypeptides or RNA. Agents that reduce these levels can potentially reduce one or more drug-related effects and/or behaviors. Conversely, agents that increase these levels can potentially enhance such drug-related effects and/or behaviors.

Accordingly, the invention provides a method of screening for an agent that inhibits or enhances a drug-related effect or behavior in which a test agent is contacted with a cell that expresses an N-type calcium channel in the absence of test agent. Preferably, the method is carried out using an in vitro assay. In such assays, the test agent can be contacted with a cell in culture or present in a tissue. Alternatively, the test agent can be contacted with a cell lysate or fraction thereof (e.g., a membrane fraction for detection of N-type calcium channels or channel subunit polypeptides). The level of (i) N-type calcium channels; (ii) channel subunit polypeptide; or (iii) channel subunit RNA is determined in the presence and absence (or presence of a lower amount) of test agent to identify any test agents that alter the level. Where channel subunit polypeptide or RNA is determined, the channel subunit is preferably N-type $Ca_v2.2$. If the level assayed is altered, the test agent is selected as a potential modulator of a drug-related effect or behavior. In a preferred embodiment, an agent that reduces the level assayed is selected as a potential inhibitor of one or more drug-related effects and/or behaviors.

Cells useful in this screening method include those from any of the species described above in connection with the method of reducing a drug-related effect or behavior. Cells that naturally express an N-type calcium channel are typically, although not necessarily, employed in this screening method. Examples include PC12 cells, SH-SY5y cells, NG108-15 cells, IMR-32 cells, SK-N-SH cells, RINm5F cells, and NMB cells. Alternatively, cells that have been engineered to express an N-type calcium channel can be used in the method.

In one embodiment, the test agent is contacted with the cell in the presence of the drug. The drug is generally one that produces one or more undesirable effects or behaviors, such as, for example, sedative-hypnotic and analgesic drugs. In particular embodiments, the drug is ethanol, a cannabinioid, or an opioid.

1. Sample

As noted above, screening assays are generally carried out in vitro, for example, in cultured cells, in a biological sample (e.g., brain, dorsal root ganglion neurons, and sympathetic ganglion neurons), or fractions thereof. For ease of description, cell cultures, biological samples, and fractions are referred to as "samples" below. The sample is generally derived from an animal (e.g., any of the research animals mentioned above), preferably a mammal, and more preferably from a human.

The sample may be pretreated as necessary by dilution in an appropriate buffer solution or concentrated, if desired. Any of a number of standard aqueous buffer solutions, employing one or more of a variety of buffers, such as phosphate, Tris, or the like, at physiological pH can be used.

2. Polypeptide-Based Assays

N-type calcium channels and/or channel subunit polypeptides can be detected and quantified by any of a number of methods well known to those of skill in the art. Examples of analytic biochemical methods suitable for detecting N-type calcium channel subunit or, in some cases, entire channels, include electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, Western blotting, and the like.

In one embodiment, N-type calcium channels are detected/quantified using a ligand binding assay, such as, for example, a radioligand binding assay. Briefly, a sample from a tissue expressing N-type calcium channels is incubated with a suitable ligand under conditions designed to provide a saturating concentration of ligand over the incubation period. After ligand treatment, the sample is assayed for radioligand binding. Any ligand that binds to N-type calcium channels can be employed in the assay, although N-type-selective calcium channel ligands are preferred. Any of the N-type calcium channel inhibitors discussed above can, for example, be labeled and used in this assay. An exemplary, preferred ligand for this purpose is $^{125}$I-ω-conotoxin GVIA. Binding of this ligand to cells can be assayed as described, for example, in Solem et al. (1997) J. Pharmacol. Exp. Ther. 282:1487-95. Binding to membranes (e.g., brain membranes) can be assayed according to the method of Wagner et al. (1995) J. Neurosci. 8:3354-3359 (see also, the modifications of this method described in McMahon et al. (2000) Mol. Pharm. 57:53-58).

In another embodiment, channel subunit polypeptide(s) are detected/quantified in an electrophoretic polypeptide separation (e.g. a 1- or 2-dimensional electrophoresis). Means of detecting polypeptides using electrophoretic techniques are well known to those of skill in the art (see generally, R. Scopes (1982) Polypeptide Purification, Springer-Verlag, N.Y.; Deutscher, (1990) Methods in Enzymology Vol. 182: Guide to Polypeptide Purification, Academic Press, Inc., N.Y.).

A variation of this embodiment utilizes a Western blot (immunoblot) analysis to detect and quantify the presence channel subunit polypeptide(s) in the sample. This technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the support with antibodies that specifically bind the target polypeptide(s). Antibodies that specifically bind to the target polypeptide(s) may be directly labeled or alternatively may be detected subsequently using labeled antibodies (e.g., labeled sheep anti-mouse antibodies) that specifically bind to a domain of the primary antibody.

In a preferred embodiment, channel subunit polypeptide(s) are detected and/or quantified in the biological sample using any of a number of well-known immunoassays (see, e.g., U.S. Pat. Nos. 4,366,241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

Conventional immunoassays often utilize a "capture agent" to specifically bind to and often immobilize the analyte (in this case a channel subunit polypeptide). In preferred embodiments, the capture agent is an antibody.

Immunoassays also typically utilize a labeling agent to specifically bind to and label the binding complex formed by the capture agent and the target polypeptide. The labeling agent may itself be one of the moieties making up the antibody/target polypeptide complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/target polypeptide complex. Other polypeptides capable of specifically binding immunoglobulin constant regions, such as polypeptide A or polypeptide G may also be used as the labeling agent. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542).

Preferred immunoassays for detecting the target polypeptide(s) are either competitive or noncompetitive. Noncompetitive immunoassays are assays in which the amount of captured target polypeptide is directly measured. In competitive assays, the amount of target polypeptide in the sample is measured indirectly by measuring the amount of an added (exogenous) polypeptide displaced (or competed away) from a capture agent by the target polypeptide present in the sample. In one competitive assay, a known amount of, in this case, labeled channel subunit polypeptide is added to the sample, and the sample is then contacted with a capture agent. The amount of labeled channel subunit polypeptide bound to the antibody is inversely proportional to the concentration of channel subunit polypeptide present in the sample.

Detectable labels suitable for use in the present invention include any moiety or composition detectable by spectroscopic, photochemical, biochemical, immunochemical, electrical, optical or chemical means. Examples include biotin for staining with a labeled streptavidin conjugate, magnetic beads (e.g., DYNABEADS magnetic beads), fluorescent dyes (e.g., fluorescein, texas red, rhodamine, coumarin, oxazine, green fluorescent protein, and the like, see, e.g., Molecular Probes, Eugene, Oregon, USA), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40 -80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

In preferred embodiments, immunoassays according to the invention are carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the invention is the Protiveris' multicantilever array. This array is based on chemo-mechanical actuation of specially designed silicon microcantilevers and subsequent optical detection of the microcantilever deflections. When coated on one side with a protein, antibody, antigen or DNA fragment, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

Antibodies useful in these immunoassays include polyclonal and monoclonal antibodies.

3. Polynucleotide-Based Assays

Changes in N-type calcium channel subunit expression level can be detected by measuring changes in levels of mRNA and/or a polynucleotide derived from the mRNA (e.g., reverse-transcribed cDNA, etc.).

Polynucleotides can be prepared from a sample according to any of a number of methods well known to those of skill in the art. General methods for isolation and purification of polynucleotides are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

i. Amplification-Based Assays

In one embodiment, amplification-based assays can be used to detect, and optionally quantify, a polynucleotide encoding a channel subunit of interest. In such amplification-based assays, the channel subunit mRNA in the sample act as template(s) in an amplification reaction carried out with a nucleic acid primer that contains a detectable label or component of a labeling system. Suitable amplification methods include, but are not limited to, polymerase chain reaction (PCR); reverse-transcription PCR (RT-PCR); ligase chain reaction (LCR) (see Wu and Wallace (1989) *Genomics* 4: 560, Landegren et al. (1988) *Science* 241: 1077, and Barringer et al. (1990) *Gene* 89: 117; transcription amplification (Kwoh et al. (1989) *Proc. Natl. Acad. Sci.* USA 86: 1173), self-sustained sequence replication (Guatelli et al. (1990) *Proc. Nat. Acad. Sci.* USA 87: 1874); dot PCR, and linker adapter PCR, etc.

To determine the level of the channel subunit mRNA, any of a number of well known "quantitative" amplification methods can be employed. Quantitative PCR generally involves simultaneously co-amplifying a known quantity of a control sequence using the same primers. This provides an internal standard that may be used to calibrate the PCR reaction. Detailed protocols for quantitative PCR are provided in PCR Protocols, A Guide to Methods and Applications, Innis et al., Academic Press, Inc. N.Y., (1990).

ii. Hybridization-Based Assays

Nucleic acid hybridization simply involves contacting a nucleic acid probe with sample polynucleotides under conditions where the probe and its complementary target nucleotide sequence can form stable hybrid duplexes through complementary base pairing. The nucleic acids that do not form hybrid duplexes are then washed away leaving the hybridized nucleic acids to be detected, typically through detection of an attached detectable label or component of a labeling system. Methods of detecting and/or quantifying polynucleotides using nucleic acid hybridization techniques are known to those of skill in the art (see Sambrook et al. supra). Hybridization techniques are generally described in Hames and Higgins (1985) *Nucleic Acid Hybridization, A Practical Approach*, IRL Press; Gall and Pardue (1969) *Proc. Natl. Acad. Sci.* USA 63: 378-383; and John et al. (1969) *Nature* 223: 582-587. Methods of optimizing hybridization conditions are described, e.g., in Tijssen (1993) *Laboratory Techniques in Biochemistry and Molecular Biology*, Vol. 24: *Hybridization With Nucleic Acid Probes*, Elsevier, N.Y.).

The nucleic acid probes used herein for detection of channel subunit mRNA can be full-length or less than the full-length of these polynucleotides. Shorter probes are generally empirically tested for specificity. Preferably, nucleic acid probes are at least about 15, and more preferably about 20 bases or longer, in length. (See Sambrook et al. for methods of selecting nucleic acid probe sequences for use in nucleic acid hybridization.) Visualization of the hybridized probes allows the qualitative determination of the presence or absence of the channel subunit mRNA of interest, and standard methods (such as, e.g., densitometry where the nucleic acid probe is radioactively labeled) can be used to quantify the level of the channel subunit polynucleotide.)

A variety of additional nucleic acid hybridization formats are known to those skilled in the art. Standard formats include sandwich assays and competition or displacement assays. Sandwich assays are commercially useful hybridization assays for detecting or isolating polynucleotides. Such assays utilize a "capture" nucleic acid covalently immobilized to a solid support and a labeled "signal" nucleic acid in solution. The sample provides the target polynucleotide. The capture nucleic acid and signal nucleic acid each hybridize with the target polynucleotide to form a "sandwich" hybridization complex.

In one embodiment, the methods of the invention can be utilized in array-based hybridization formats. In an array format, a large number of different hybridization reactions can be run essentially "in parallel." This provides rapid, essentially simultaneous, evaluation of a number of hybridizations in a single experiment. Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211).

Arrays, particularly nucleic acid arrays, can be produced according to a wide variety of methods well known to those of skill in the art. For example, in a simple embodiment, "low-density" arrays can simply be produced by spotting (e.g. by hand using a pipette) different nucleic acids at different locations on a solid support (e.g. a glass surface, a membrane, etc.). This simple spotting approach has been automated to produce high-density spotted microarrays. For example, U.S. Pat. No. 5,807,522 describes the use of an automated system that taps a microcapillary against a surface to deposit a small volume of a biological sample. The process is repeated to generate high-density arrays. Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high-density oligonucleotide microarrays. Synthesis of high-density arrays is also described in U.S. Pat. Nos. 5,744,305; 5,800,992; and 5,445,934.

In a preferred embodiment, the arrays used in this invention contain "probe" nucleic acids. These probes are then hybridized respectively with their "target" nucleotide sequence(s) present in polynucleotides derived from a biological sample. Alternatively, the format can be reversed, such that polynucleotides from different samples are arrayed and this array is then probed with one or more probes, which can be differentially labeled.

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials that can be employed include paper, ceramics, metals, metalloids, semiconductive materials, and the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, and/or enhance signal detection. If covalent bonding between a compound and the surface is desired, the surface will usually be polyfunctional or be capable of being polyfunctionalized. Functional groups that may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

Arrays can be made up of target elements of various sizes, ranging from about 1 mm diameter down to about 1 µm. Relatively simple approaches capable of quantitative fluorescent imaging of 1 cm$^2$ areas have been described that permit acquisition of data from a large number of target elements in a single image (see, e.g., Wittrup (1994) *Cytometry* 16:206-213, Pinkel et al. (1998) *Nature Genetics* 20: 207-211).

Hybridization assays according to the invention can also be carried out using a MicroElectroMechanical System (MEMS), such as the Protiveris' multicantilever array.

iii. Polynucleotide Detection

Channel subunit RNA is detected in the above-described polynucleotide-based assays by means of a detectable label. Any of the labels discussed above can be used in the polynucleotide-based assays of the invention. The label may be added to a probe or primer or sample polynucleotides prior to, or after, the hybridization or amplification. So called "direct labels" are detectable labels that are directly attached to or incorporated into the labeled polynucleotide prior to conducting the assay. In contrast, so called "indirect labels" are joined to the hybrid duplex after hybridization. In indirect labeling, one of the polynucleotides in the hybrid duplex carries a component to which the detectable label binds. Thus, for example, a probe or primer can be biotinylated before hybridization. After hybridization, an avidin-conjugated fluorophore can bind the biotin-bearing hybrid duplexes, providing a label that is easily detected. For a detailed review of methods of the labeling and detection of polynucleotides, see *Laboratory Techniques in Biochemistry and Molecular Biology*, Vol. 24: *Hybridization With Nucleic Acid Probes*, P. Tijssen, ed. Elsevier, N.Y., (1993)).

The sensitivity of the hybridization assays can be enhanced through use of a polynucleotide amplification system that multiplies the target polynucleotide being detected. Examples of such systems include the polymerase chain reaction (PCR) system and the ligase chain reaction (LCR) system. Other methods recently described in the art are the nucleic acid sequence based amplification (NAS-BAO, Cangene, Mississauga, Ontario) and Q Beta Replicase systems.

In a preferred embodiment, suitable for use in amplification-based assays of the invention, a primer contains two fluorescent dyes, a "reporter dye" and a "quencher dye." When intact, the primer produces very low levels of fluorescence because of the quencher dye effect. When the primer is cleaved or degraded (e.g., by exonuclease activity of a polymerase, see below), the reporter dye fluoresces and is detected by a suitable fluorescent detection system. Amplification by a number of techniques (PCR, RT-PCR, RCA, or other amplification method) is performed using a suitable DNA polymerase with both polymerase and exonuclease activity (e.g., Taq DNA polymerase). This polymerase synthesizes new DNA strands and, in the process, degrades the labeled primer, resulting in an increase in fluorescence. Commercially available fluorescent detection systems of this type include the ABI Prism® Systems 7000, 7700, or 7900 (TaqMan®) from Applied Biosystems or the LightCycler® System from Roche.

D. Screening Based on Level of Calcium Current

The invention also provides a screening method based on determining the effect, if any, of a test agent on the level of the depolarization-induced inward calcium current mediated by N-type calcium channels. Agents that reduce this current can potentially reduce one or more drug-related effects and/or behaviors. Conversely, agents that increase this current can potentially enhance such drug-related effects and/or behaviors.

Accordingly, the invention provides a method of screening for an agent that inhibits or enhances a drug-related effect or behavior in which a test agent is contacted with a cell that expresses an N-type calcium channel in the absence of test agent. Preferably, the method is carried out using an in vitro assay. In such assays, the test agent can be contacted with a cell in culture or present in a tissue. Alternatively, the test agent can be contacted with channels in in synaptoneurosomes or purified channel proteins reconstitued in lipid bilayers. The level of depolarization-induced inward calcium current is determined in the presence and absence (or presence of a lower amount) of test agent to identify any test agents that alter the level. If the level of the calcium current is altered, the test agent is selected as a potential modulator of a drug-related effect or behavior. In a preferred embodiment, an agent that reduces the calcium current is selected as a potential inhibitor of one or more drug-related effects and/or behaviors.

The calcium current can be measured using any available technique An indirect measurement of calcium current can be carried out described by McMahon et al. (2000) Mol. Pharm. 57:53-58). In this method, cells are loaded with a dye that fluoresces in the presence of calcium (such as fura-2 AM) prior to depolarization. Cells are generally also preincubated in the presence or absence of an N-type calcium channel-specific inhibitor (e.g., 1 µM ω-conotoxin GVIA) to determine the extent of the calcium current that is attributable to N-type calcium channels. Cells are subsequently depolarized by incubation in a 50 mM KCl buffer in the continued presence or absence of the inhibitor. The resulting calcium current can then be calculated based on fluorescence, as described by Solem et al. (1997) J. Pharmacol. Exp. Ther. 282:1487-95. Ruiz-Velasco and Ikeda (J. Neuroscience (2000) 20:2183-91 describe the direct measurement of calcium currents using a whole-cell variant of the patch-claim technique, which can also be employed in the present invention.

Cells useful for screening based on calcium current include any of those described above in connection with screening based levels of N-type calcium channels or channel subunit polypeptides or RNA.

In one embodiment, the test agent is contacted with the cell in the presence of the drug. The drug is generally one that produces one or more undesirable effects or behaviors, such as, for example, sedative-hypnotic and analgesic drugs. In particular embodiments, the drug is ethanol, a cannabinioid, or an opioid.

E. Test Agent Databases

In a preferred embodiment, generally involving the screening of a large number of test agents, the screening method includes the recordation of any test agent selected in any of the above-described prescreening or screening methods in a database of agents that may modulate a drug-related effect or behavior.

The term "database" refers to a means for recording and retrieving information. In preferred embodiments, the database also provides means for sorting and/or searching the stored information. The database can employ any convenient medium including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems," mainframe systems, distributed nodes on an inter- or intra-net, data or databases stored in specialized hardware (e.g. in microchips), and the like.

F. Test Agents Identified by Screening

When a test agent is found to alter the level of N-type calcium channels, channel subunit polypeptide or RNA, or depolarization-induced inward calcium current, a preferred screening method of the invention further includes combining the test agent with a carrier, preferably pharmaceutically acceptable carrier, such as are described above. Generally, the concentration of test agent is sufficient to alter the level of N-type calcium channels, channel subunit polypeptide or RNA, or depolarization-induced inward calcium current when the composition is contacted with a cell. This concentration will vary, depending on the particular test agent and specific application for which the composition is intended. As one skilled in the art appreciates, the considerations affecting the formulation of a test agent with a carrier are generally the same as described above with respect to methods of reducing a drug-related effect or behavior.

In a preferred embodiment, the test agent is administered to an animal to measure the ability of the selected test agent to modulate a drug-related effect or behavior in a subject, as described in greater detail below.

G. Screening for Modulation of a Drug-Related Effect or Behavior

The invention also provides a method of screening for an agent that that modulates a drug-related effect or behavior in a subject. The method entails selecting an N-type calcium channel modulator as a test agent, and measuring the ability of the selected test agent to modulate a drug-related effect or behavior in a subject. Any agent that modulates N-type calcium channels that can be administered to a subject can be employed in the method. Modulators selected through any of the prescreening or screening methods of the invention can be tested for modulation of drug-related effects or behavior. Alternatively, known N-type channel modulators can be employed. In a preferred embodiment, the selected test agent is an N-type calcium channel inhibitor.

Test agents can be formulated for administration to a subject as described above for N-type calcium channel inhibitors.

The subject of the method can be any individual that has N-type calcium channels and in which drug-related effects or behaviors can be measured. Examples of suitable subjects include research animals, such as *Drosophila melanogaster*, mice, rats, guinea pigs, rabbits, cats, dogs, as well as monkeys and other primates, and humans. In preferred embodiments, an animal model established for studying particular drug-related effects or behaviors is employed. Exemplary animal models for studying the effects and behaviors associated with ethanol are described in the Examples below.

The test agent is administered to the subject before, during, and/or after administration of the drug of interest, and the subject is tested or observed to determine whether the test agent modulates a particular drug-related effect or behavior. Test agents can be administered by any suitable route, as described above for N-type calcium channel inhibitors. Generally, the concentration of test agent is sufficient to alter the level of N-type calcium channels, channel subunit polypeptide or RNA, or depolarization-induced inward calcium current in vivo.

The drug and drug-related effect or behavior studied can be any of those described above. The drug is administered by any suitable route and in an amount sufficient to produce the drug-related effect or behavior under examination. The drug-related effect or behavior is measured and compared with that observed in the absence of test agent and/or in the presence of a lower amount of test agent.

Method of Assessing Risk of Drug-Related Effects or Behaviors

Another aspect of the invention is a method of assessing a subject's risk for experiencing a drug-related effect or developing a drug-related behavior. The method entails measuring one of several N-type calcium channel-related parameters in a biological sample from the subject. Suitable parameters include the levels of N-type calcium channels, channel subunit polypeptides (e.g., N-type $Ca_v2.2$ subunit polypeptide), channel subunit RNA (e.g., N-type $Ca_v2.2$ subunit RNA), and depolarization-induced inward calcium current. The considerations affecting sample preparation and assay are as described above, with the additional consideration that sample collection is preferably minimally invasive to the subject.

The risk for experiencing a drug-related effect or developing a drug-related behavior is directly correlated with each of these levels. To determine whether the subject has a normal, elevated, or reduced risk, the level measured for the selected N-type calcium channel parameter is compared to that of an appropriate matched (e.g., for age, sex, etc.) control population. The control population can be representative of the general population to allow a determination of risk of the individual subject as compared to, for example, the average risk in the general population.

If a subject is determined to have a high risk for experiencing a drug-related effect or developing a drug-related behavior, an N-type calcium channel inhibitor can be administered to the subject to reduce this risk. Preferably, the inhibitor dose is sufficient to reduce the levels N-type calcium channels, channel subunit polypeptides (e.g., N-type $Ca_v2.2$ subunit polypeptide), channel subunit RNA (e.g., N-type $Ca_v2.2$ subunit RNA), and/or depolarization-induced inward calcium current to within a normal range (i.e., the range observed in the control population).

Kits

The invention also provides kits useful in practicing the methods of the invention. In one embodiment, a kit of the invention includes an N-type calcium channel inhibitor in a suitable container. In a variation of this embodiment, the N-type calcium channel inhibitor is formulated in a pharmaceutically acceptable carrier. The kit preferably includes instructions for administering the N-type calcium inhibitor to a subject to reduce or prevent a drug-related effect or behavior.

In another embodiment, the kit is a diagnostic kit for use in assessing a subject's risk for experiencing a drug-related effect or developing a drug-related behavior. The kit includes at least one component that specifically binds to N-type calcium channels, N-type $Ca_v2.2$ subunit polypeptides, or N-type $Ca_v2.2$ subunit RNA. This binding component can be used to detect the presence of its binding partner in a biological sample from the subject. In a preferred embodiment, the binding component is labeled with a detectable label or, alternatively, the kit includes a labeling component that is capable of binding to, and thereby labeling, the binding component when the diagnostic method of the invention is carried out. The kit preferably includes instructions for carrying out the diagnostic method of the invention.

Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

The following examples are offered to illustrate, but not to limit, the claimed invention.

Example 1

Voluntary Ethanol Consumption and Preference in Mice Lacking the N-Type $Ca_v2.2$ Subunit Exposure to 25-200 mM ethanol for 2-8 days was previously shown to produce a reversible time- and concentration-dependent increase in binding sites for the N-type calcium channel antagonist $^{125}$I-ω-conotoxin GVIA in the neural cell line PC12. This increase is associated with increased inhibition by ω-conotoxin GVIA of depolarization-evoked rises in intracellular $Ca^{2+}$. Ethanol-induced increases in o)-conotoxin GVIA binding are blocked in cells expressing a fragment of PKCε (εV1) that inhibits PKCε translocation and function. McMahon et al. (2000) Mol. Pharm. 57:53-58. To investigate whether N-type calcium channels modulate ethanol-related effects and behaviors in vivo, mice lacking the $Ca_v2.2$ subunit of N-type calcium channels were given ethanol and subjected to tests designed to measure various different ethanol-related effects and behaviors.

Mice

The generation of mice lacking $Ca_v2.2$ has been described previously (Kim et al., 2001). Mice used in this and subsequent examples were (unless indicated otherwise) F1 generation C57BU6Jx129/SvJae hybrids, generated by crossing heterozygous inbred 129/SvJae and N10 C57BU6 mice. The mice were obtained from BioGenomics, Inc. (Seoul, South Korea). Mutant and wild-type mice were housed together in standard Plexiglas cages with food and water available ad libitum. The colony room was maintained on a 12:12 hour light:dark cycle with lights on at 06:00 a.m. Mice were between the ages of two and six months at the time of testing. Animal care and handling procedures were in accordance with institutional and National Institutes of Health guidelines. All experiments were performed with male mice.

Voluntary Ethanol Consumption and Preference

Since antagonists of L-type calcium channels reduce ethanol consumption in several animal species (Rezvani and Janowsky, 1990; Rezvani et al., 1991; Fadda et al., 1992; De Beun et al., 1996), ethanol self-administration was assessed in mice that lack N-type channels. Voluntary ethanol consumption and preference were tested using a two-bottle choice paradigm. Baseline fluid consumption was monitored by allowing the animals access to two bottles, both containing water only, for four days prior to the experiment. Mice were then allowed free access to two drinking bottles, one containing ethanol solution and the other containing water. Bottles and mice were weighed every 2-days to monitor consumption. The side of the cage upon which the ethanol bottle was presented (left vs. right) was switched every 2 days. The starting concentration of ethanol was 3 percent (volume/volume). This concentration was increased every fourth day to 6, 10, 14, and 20%. Ethanol preference was calculated by dividing volume of ethanol consumed (ml/day) by total volume of fluid consumed (ml/day) and multiplying by 100%. Data were compared by two-way ANOVA with a repeated-measure for ethanol concentration and a factor for genotype.

To control for possible differences in taste preference, the same protocol was followed for saccharin (0.03% or 0.06%) and quinine (0.015 mM or 0.030 mM) solutions except that mice were allowed 2-day access to each concentration, and the side on which the tastant was presented was switched daily. Ethanol, quinine, and saccharin solutions were made in tap water.

Results $Ca_v2.2$ null mice showed decreased alcohol consumption and reduced alcohol preference compared with wild-type littermates when provided solutions containing 6% or 10% ethanol (FIGS. 1A and B). Consumption declined at higher ethanol concentrations in both genotypes. There were no differences in water consumption (FIG. 1C) or intake of quinine- or saccharin-containing solutions (FIG. 1D). Thus, reduced intake in $Ca_v2.2$ null mice appeared specific for ethanol. Baseline 24-h water consumption was also monitored by allowing mice access to two water bottles. No genotypic differences were seen, consistent with a previous report that water and food consumption are normal in $Ca_v2.2$ null mice (Beuckmann et al., 2003).

Example 2

Ethanol Reward in Mice Lacking the N-Type $Ca_v2.2$ Subunit $Ca_v2.2$ null mice may consume less ethanol than wild-type mice because they find it less rewarding. To investigate this possibility, ethanol-induced place conditioning, which measures an animal's preference for a context associated with administration of a drug (Tzschentke, 1998), was measured.

Place Conditioning

Mice were trained in a conditioned place preference (CPP) apparatus (Med Associates, St. Albans, Vt.) that consisted of white and black chambers with different floor textures (black side with rod floor vs. white side with grid floor) that were separated by a central gray access compartment. To measure baseline preference for the test chambers, mice were allowed to roam freely in the entire apparatus for 30 min during the first day of the test. Both genotypes showed a slight baseline preference for the black chamber, and so equal numbers of mice were conditioned to ethanol in either colored test chamber. The ethanol-paired chamber was assigned randomly across subjects. For conditioning, mice were treated with ethanol (1.2, 2.0, or 2.8 grams/kg v/v in 0.9% saline) and immediately placed in one side for 5 min. On the next day, they were injected with an equivalent volume of saline and placed in the other side. This sequence was repeated four times for a total of 4 days ethanol and 4 days saline, with two rest days halfway through training. On the test day immediately following the final training day, mice were allowed free access to all 3 compartments for 30 min. CPP was assessed by comparing the time spent in the drug-paired chamber on the test day with the time spent in the saline-paired chamber and the central chamber on the test day by paired two-tailed t-tests with Bonferroni correction for multiple comparisons. The mice were considered to have developed CPP for ethanol if they spent more time in the ethanol-paired chamber compared with the other two chambers on the test day.

Results

Figure 2:
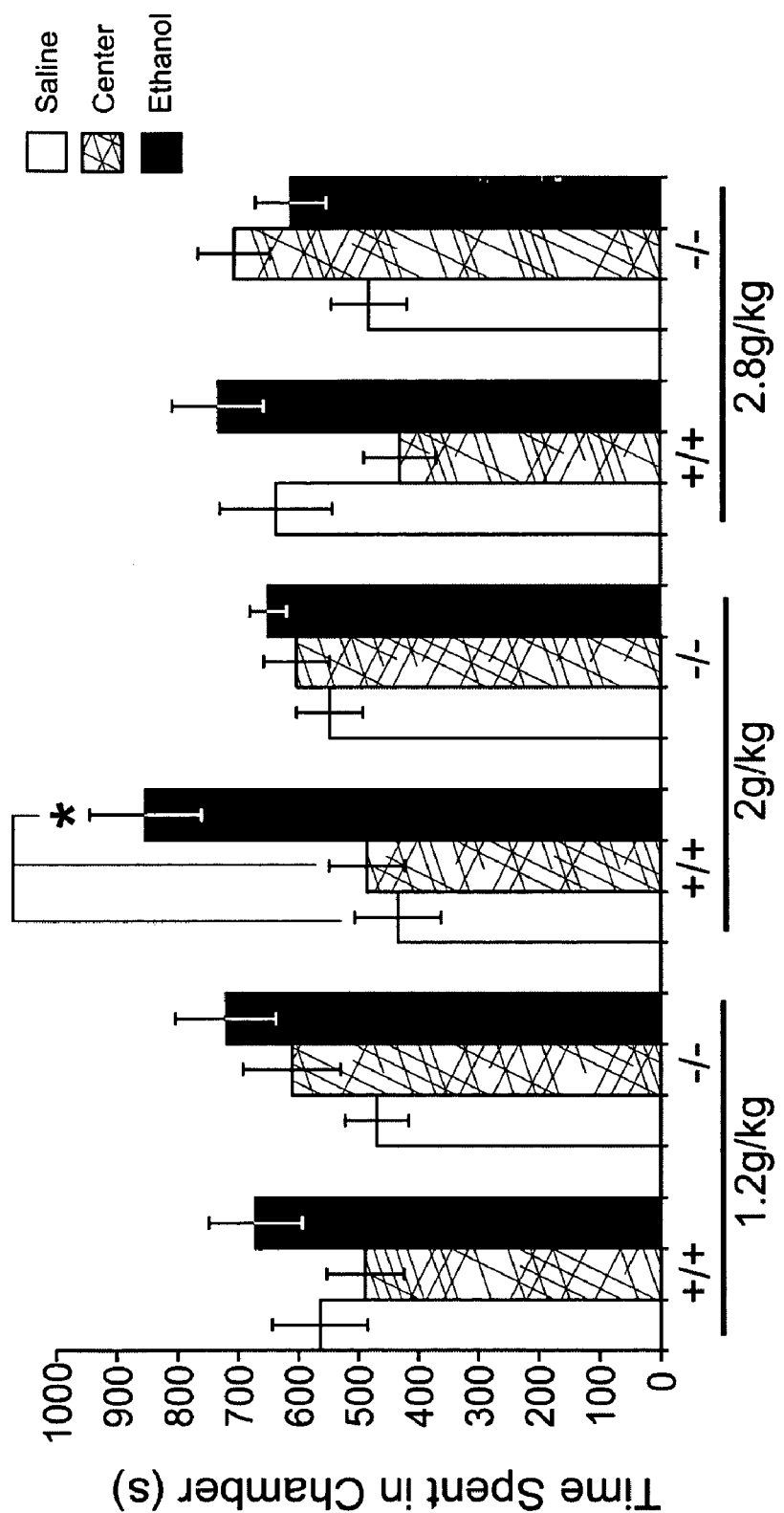
FIG. 2 shows the results of an ethanol-induced place conditioning study. See Example 2. Mice were injected intraperitoneally with saline and placed in the central, access chamber of a three-chambered apparatus. The door to a second chamber (saline-paired chamber), off the central chamber, was then opened to allow mice access to the second chamber, into which the mice entered. The door was then closed and the mice remained in the second chamber for 5 min before being removed and returned to the home cage. On the following day, the procedure was repeated, except that the mice were given an intraperitoneal injection of ethanol (at the doses indicated in FIG. 2) and allowed to enter, by the same procedure as for the saline-paired side, a third chamber (drug-paired chamber), instead of the saline-paired chamber. The ethanol and saline-paired chambers differed in floor texture and wall color. Drug-paired and saline-paired chambers were assigned randomly, i.e., some mice received ethanol in the same type of chamber in which other mice received saline. This process, saline one day and ethanol the next, was then repeated three times further, resulting in a total of four saline/drug-chamber pairings. On the day immediately following the completion of this 8-day training period, the mice were placed into the central chamber and allowed free access to all three chambers for a total of 30 minutes. Time spent in each of the three chambers was analyzed for each genotype by paired two-tailed t-tests with Bonferroni correction for multiple comparisons. Conditioned Place Preference (CPP) was defined as a mouse spending significantly longer in the drug-paired chamber versus the two other chambers during the 30-min test. $Ca_v2.2$ null mice (KO) do not show CPP at 2 g/kg ethanol, whereas wild-type mice show a robust CPP; $P<0.02$ compared with the saline-paired chamber and $P<0.03$ compared with the central chamber at same dose of 2 gram/kg ethanol. Neither genotype showed significant CPP at the other doses tested. n=10-14 mice per genotype. To control for a baseline preference for a particular chamber type, all mice received a 30-min test in the chambers prior to training. There was no difference between the genotypes.

When trained with 2 g/kg ethanol, a dose that establishes strong place preference in normal mice (Risinger et al., 2001; Dickinson et al., 2003), wild-type mice showed a robust place preference for ethanol that was completely absent in $Ca_v2.2$ null mice (FIG. 2). In order to control for altered acute sensitivity to ethanol (FIG. 1), the ability of a low (1.2 g/kg) and a high (2.8 g/kg) dose of ethanol to produce place preference was assayed. Neither genotype showed place preference or aversion at these doses. These data suggest that in the absence of functional N-type calcium channels, ethanol is not rewarding.

Example 3

Loss of Righting Reflex in Mice Lacking the N-Type $Ca_v2.2$ Subunit

To examine whether N channels contribute to manifestations of ethanol intoxication, ethanol-induced loss of the righting reflex (LORR) was measured in $Ca_v2.2$ null mice and wild-type littermates.

Loss of Righting Reflex

Both groups of mice were injected intraperitoneally with ethanol (3.6 g/kg in 0.9% w/v saline) and then assessed for loss of the righting reflex (LORR). Loss of the righting reflex was defined as a mouse being unable to right itself 3 times within 30 sec. Upon losing the righting reflex, mice were placed on their backs and the time taken for them to regain the righting reflex was measured. A mouse was defined as having regained the righting reflex when it was able to right itself 3 times within 30 sec. A blood sample was taken from the tail of each mouse when it regained the righting reflex in order to determine blood ethanol concentration. Blood was centrifuged at 10,000 g and serum blood alcohol concentration determined using an Analox AM-1 analyser (Analox Instruments, Luneburg Mass.).

LORR Threshold

We determined the threshold concentration of ethanol required to induce LORR using the "up-and-down" method (Dixon, 1965; Findlay et al., 2002). A mouse was given an intraperitoneal injection of 10% v/v ethanol in saline, and 5 min later tested for LORR of greater than 1 minute. If the first mouse lost the righting reflex, then the next mouse was given a lower ethanol dose. If the first mouse did not lose the righting reflex, then the next mouse was given a higher dose. The log dose interval was 0.0138, corresponding to approximately a 0.1 g/kg difference between doses. The ED50 value was determined as described (Findlay et al., 2002), with 95% confidence intervals determined by the following equation: 95% CI=dosing increment×square root of $(2/n) \times 1.96$, where n=the last n trials (6) and 1.96 reflects the 0.05 $\alpha$ level (Dixon, 1965).

Ethanol Clearance

Mice were injected intraperitoneally with 4 g/kg ethanol in 0.9% (w/v) saline. A 20 µl blood sample was taken from the tail at 10, 30, 60, 120 and 180 min following the ethanol injection in order to determine blood ethanol concentrations.

Figure 3:
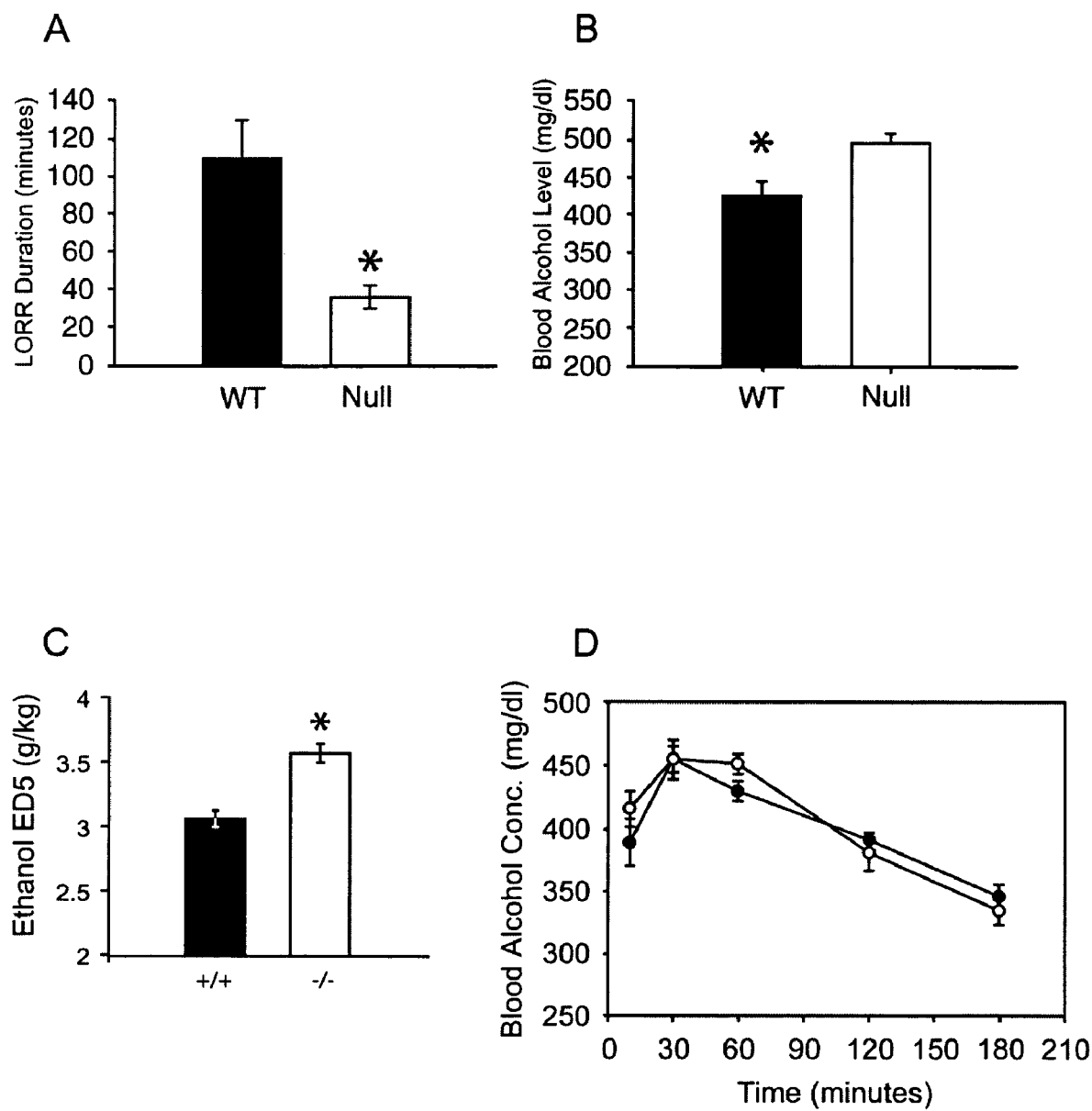
FIG. 3A-D show the results of a loss of righting reflex (LORR) study. See Example 3. Open circles or bars indicate the results for $Ca_v2.2$ null mice; closed circles or bars indicate the results for wild-type mice.

Results $Ca_v2.2$ null mice showed a shorter duration of the LORR for a hypnotic dose of ethanol and regained their righting reflex at a higher blood ethanol concentration than wild-type littermates (FIGS. 3A and B). Differences in LORR duration may reflect altered initial sensitivity, or altered development of acute tolerance to ethanol. To specifically assay for differences in initial sensitivity, we determined the threshold dose of ethanol required to produce LORR in the two genotypes (Dixon, 1965; Findlay et al., 2002). The threshold dose in $Ca_v2.2$ null mice was significantly higher than in wild-type mice (FIG. 3C). There was no difference between the genotypes in the clearance of ethanol from the blood following injection of 4 g/kg ethanol, demonstrating that $Ca_v2.2$ null mice do not show altered ethanol metabolism (FIG. 3D). These results show that sensitivity to the hypnotic effect of ethanol is reduced in $Ca_v2.2$ null mice.

Example 4

Motor Incoordination in Mice Lacking the N-Type Ca$_v$2.2 Subunit

Studies using inbred mouse lines have shown that sensitivity to the hypnotic and ataxic effects of ethanol are not directly correlated (Dudek and Phillips, 1990; Pucilowski et al., 1996). To assess an acute response to low doses of ethanol, ethanol-induced motor incoordination (ataxia) was measured on a rotarod, first operating at a constant velocity of 20 rpm and then accelerating.

Rotarod

Mice were trained to remain for 180 s on a rotarod apparatus (Ugo Basile Biological Research, Varese, Italy) rotating at a fixed rate of 20 rpm. The first test session was carried out the following day. During a test session, each mouse was placed on the rotarod and the time taken for the animal to fall off the rod was recorded. Mice were then injected intraperitoneally with ethanol and re-tested every 15 min for 1 h. Mice were tested on a fixed-rate rotarod after 1.5 g/kg ethanol in the first test session, then 2 g/kg ethanol 3 days later. Three further days later, the mice were trained to remain on an accelerating (4-40 rpm) rotarod for 300s. On a subsequent day, they were trained once further and then given an intraperitoneal injection of ethanol (2 gram/kg), and tested every 15 minutes for their ability to stay on the rotarod.

Results

Figure 4A:
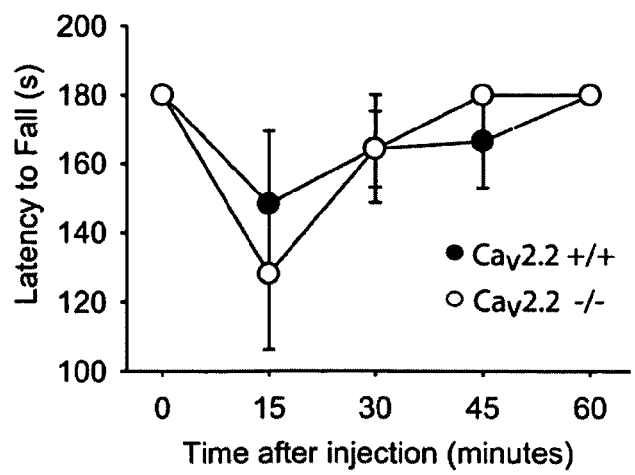
FIG. 4A-C shows the results of a study of ethanol-induced motor incoordination conducted using a rotarod that rotated at constant velocity of 20 rpm (FIGS. 4A and B) or that accelerated (FIG. 4C). See Example 4. Open circles indicate the results for $Ca_v2.2$ null mice; closed circles indicate the results for wild-type mice.
Figure 4B:
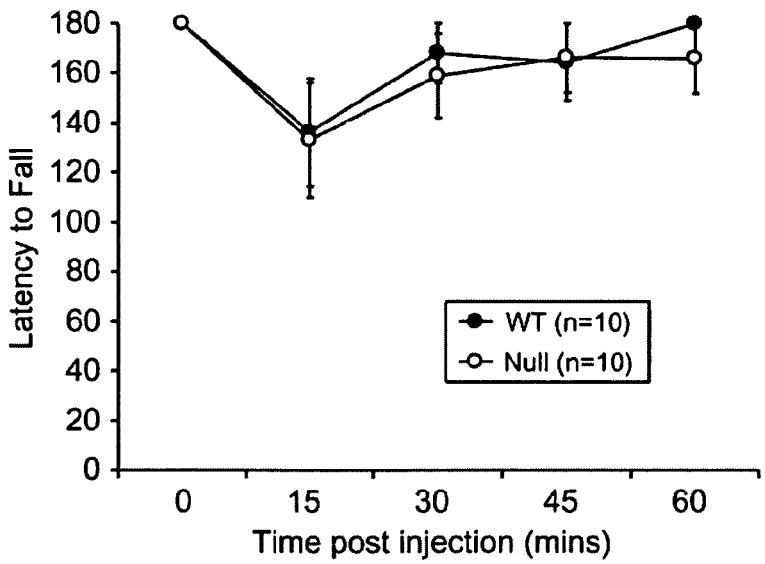
Figure 4C:
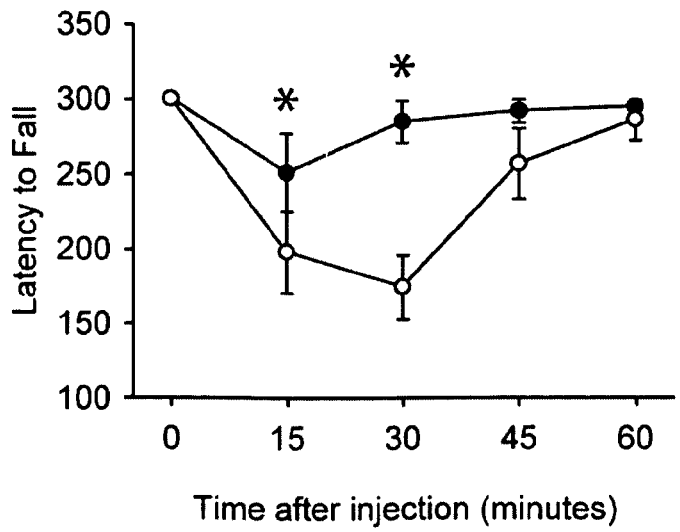

All mice were successfully trained to stay on a fixed rate (20 rpm) rotarod for 180 s after 2-3 trials. Mice of both genotypes showed a similar decrease in latency to fall from the fixed-rate rotarod following injection of either 1.5 g/kg or 2 g/kg ethanol (FIGS. 4A and B). Thus, there were no significant differences between the two groups with respect to ability to remain on the constant-velocity rotarod. To increase the difficulty of the test, we also examined mice placed on an accelerating rotarod following injection of 2 g/kg ethanol (i.p. in 0.9% w/v saline). Before injection, all mice were able to remain on the accelerating rotarod, but after ethanol injection, Ca$_v$2.2 null mice showed a shorter latency to fall compared with wild-type mice (FIG. 4C). Ca$_v$2.2 null mice thus appeared more sensitive than wild-type littermates to the ataxic effects ethanol. The opposite effects of the null mutation on ethanol-induced ataxia and hypnosis likely reflect different roles for N-type calcium channels in regulating the neural circuits involved in alertness and motor control.

Example 5

Alcohol Withdrawal in Mice Lacking the N-Type Ca$_v$2.2 Subunit

Figure 5:
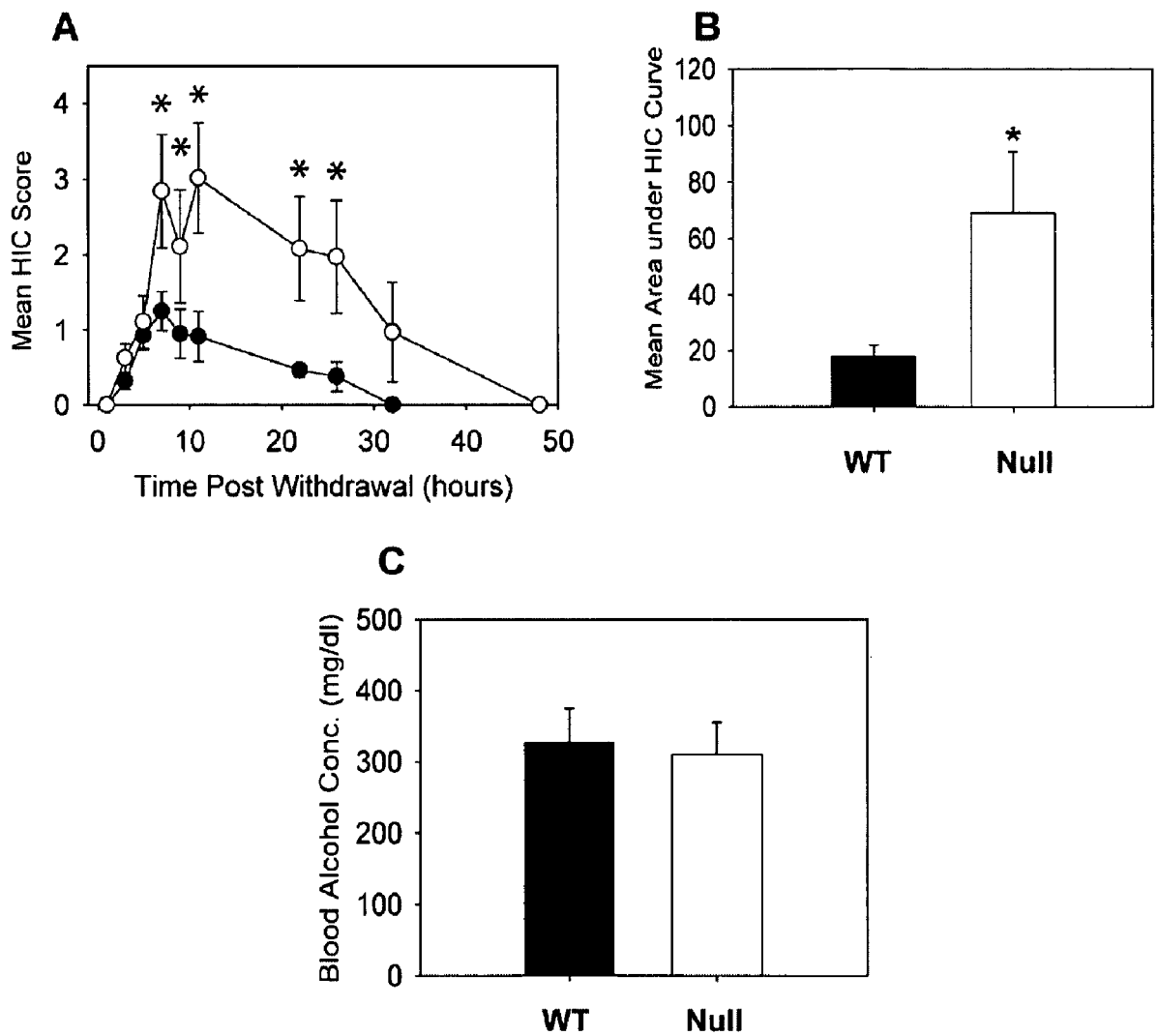
FIG. 5A-C show the results of a study of handling-induced convulsions after alcohol withdrawal. See Example 5. Mice were exposed to alcohol vapor for 3 days, 16 hours per day, to induce ethanol dependence and then removed from the vapor chambers. Handling-induced convulsions (HIC) were measured at various intervals over the next 48 hours. Open circles or bars indicate the results for $Ca_v2.2$ null mice; closed circles or bars indicate the results for wild-type mice.

Alcohol withdrawal is associated with seizures, and may be mediated in part by upregulation of at least 2 kinds of excitatory ion channels, NMDA receptor-gated channels and L-type calcium channels. Since chronic ethanol exposure up-regulates N-type calcium channels in rat brain, N-type calcium channels mediate calcium entry into neurons, and calcium promotes neuronal depolarization and excitability, the possibility that absence of N channels might reduce alcohol withdrawal seizures was examined. Ca$_v$2.2 null mice and littermates were exposed to alcohol vapor for 3 days, 16 hours per day, to induce ethanol dependence, and then removed from the vapor chambers. Handling-induced convulsions were measured at several intervals by blind observers over the next 48 hours according to the criteria in the Table 1 below. Ca$_v$2.2 null mice showed increased handling-induced convulsions during alcohol withdrawal (FIG. 5).

TABLE 1

| Score | Behavior |
| --- | --- |
| 0 | No convulsions. |
| 1 | Tonic convulsion(s) elicited by single 360-degree tail rotation. |
| 2 | Tonic-clonic convulsion elicited by single 360-degree tail rotation. |
| 3 | Prolonged (>5 sec) repetitive tonic-clonic convulsions elicited by single 360-degree tail spin. |
| 4 | Tonic convulsion elicited when lifted by tail usually followed by repetitive tonic-clonic convulsions. |
| 5 | Tonic-clonic convulsion elicited when lifted by tail, onset usually delayed by 2–3 sec. |
| 6 | Prolonged (>5 s) repetitive tonic-clonic convulsions when lifted by the tail. |
| 7 | Convulsion elicited by removal of cage top, before lifting by tail. |

Example 6

Conditioned Taste Aversion in Mice Lacking the N-Type Ca$_v$2.2 Subunit

In addition to its rewarding properties, acute ethanol exposure has aversive effects, which can also be assayed using classical conditioning paradigms (Cunningham and Henderson, 2000). Having established that the rewarding effects of ethanol are absent in Ca$_v$2.2 null mice, the aversive properties of ethanol were investigated using a conditioned taste aversion assay with ethanol as the unconditioned stimulus and 1.2% NaCl as the conditioned stimulus (Risinger and Boyce, 2002; Chester et al., 2003).

Conditioned Taste Aversion

The conditioned taste aversion study was carried out according to established protocols (Risinger and Boyce, 2002) (Chester et al., 2003). Animals were singly housed and acclimatized to limited water access by allowing them access to water for decreasing periods of time (10, 8, 6 and 4 h per day on subsequent days) followed by 2-h daily access for one week. Following acclimatization, they were placed on the conditioning schedule consisting of 1-h access (13:00 to 14:00h) to the conditioned stimulus (CS, a solution of 1.2% (w/v) saline), followed immediately by a saline (0.9% w/v) injection. Later that same day (19:00 to 20:00 h) they were allowed access to drinking water. The following day they were allowed two hours of access to drinking water (13:00 to 15:00). This 2-d procedure constituted a single trial and was repeated 7 times to establish baseline consumption levels of 1.2% NaCl. Seven additional trials were then conducted using a 2 g/kg ethanol injection in place of saline. Data were compared by two-way ANOVA with factors for injection and genotype.

Results

Figure 6:
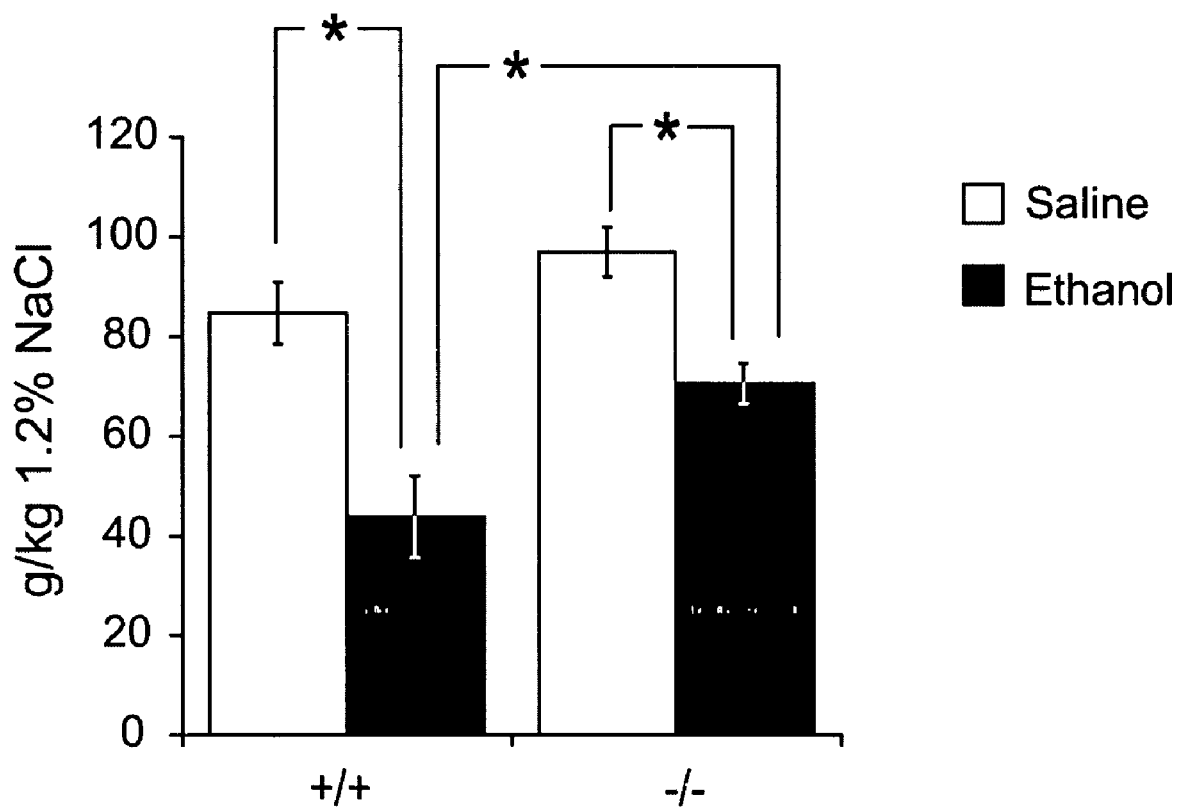
FIG. 6 indicates that ethanol conditioned taste aversion was reduced in $Ca_v2.2$ null mice compared with wild-type mice. See Example 6. Data shown are mean consumption of 1.2% NaCl during 1-hour daily sessions for 7 days following injection of saline and then for another 7 days following injection of ethanol (2 g/kg i.p.). Two-way ANOVA showed significant effects of treatment (F[1,36]=31.007, p<0.01) and genotype (F[1,36]=10.321, p=0.03), with a post hoc Bonferroni test revealing significant differences between wild-type and $Ca_v2.2$ null mice only during ethanol treatment (P=0.004).

There was no difference in baseline consumption of 1.2% NaCl following a control saline injection. Upon commencement of ethanol treatment, both genotypes rapidly developed conditioned taste aversion, but the magnitude of this aversion was reduced in the Cav-2.2 null mice when compared to their wild-type littermates (FIG. 6), indicating that the Ca$_v$2.2 null mice find ethanol less aversive.

Example 7

Influence of Genetic Background

Figure 7:
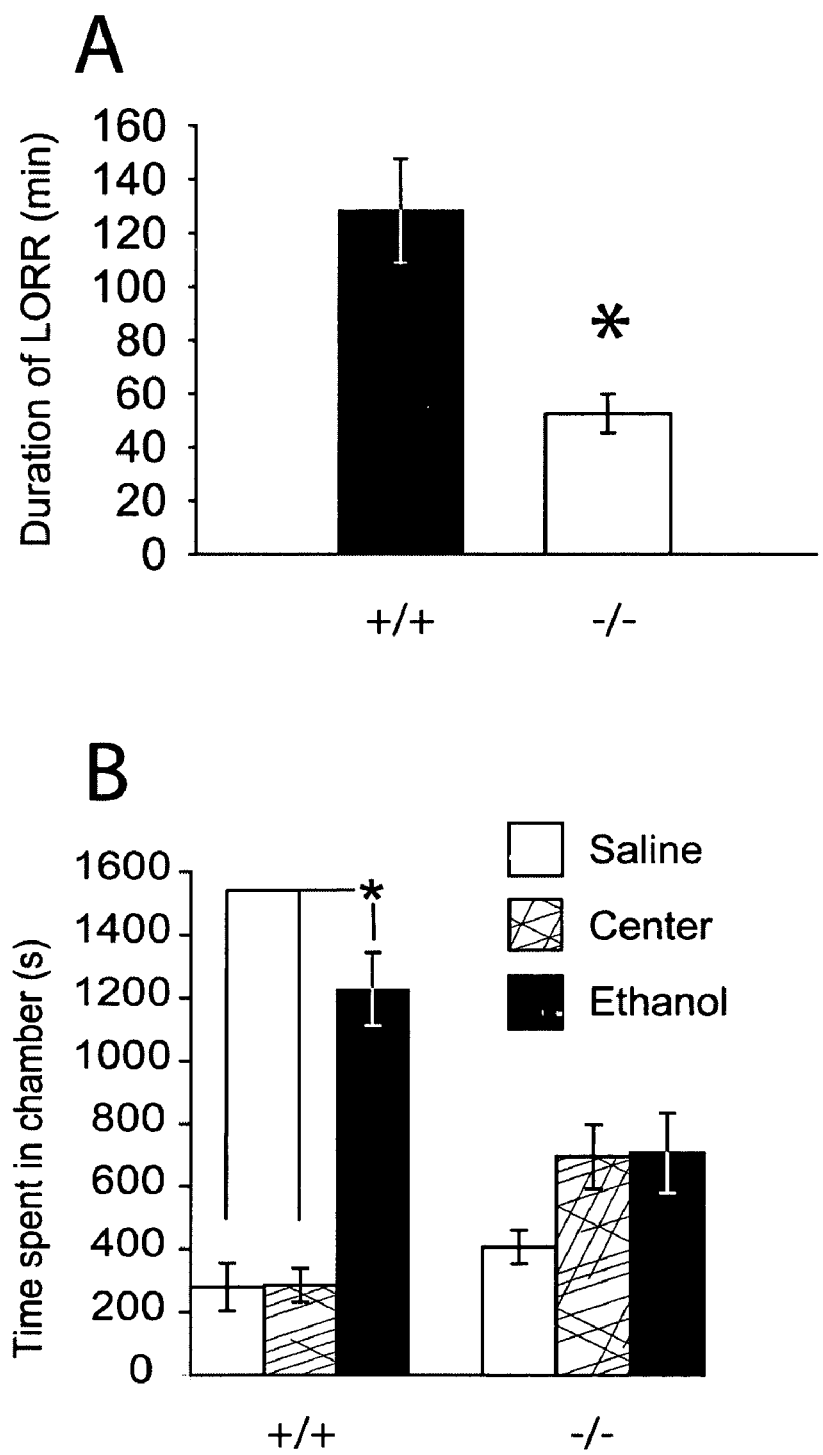
FIGS. 7A and B show ethanol-induced LORR and conditioned place preference in $Ca_v2.2$ null mice on an inbred 129/SvJae background. See Example 7.
FIG. 7B indicates that ethanol (1.5 g/kg) induced a significant conditioned place preference in wild-type but not in $Ca_v2.2$ null mice. Data were analyzed by one-way paired two-tailed t-test with Bonferroni correction for multiple comparisons. *P<0.05.

The expression of ethanol-related behaviors in mutant mouse lines can be influenced by the genetic background (Bowers et al., 1999). The mice used in the above experiments were F1 hybrids generated from heterozygote mice on inbred C57BU6J and 129 SvJae backgrounds. Since the embryonic stem cells (J1) used to generate the original chimeras were originally derived from strain 129/SvJae, there still remained a slight possibility that the $Ca_v2.2$ null phenotype might be due to co-segregation of neighboring genes derived from the 129/SvJae background, and not a consequence of the null mutation. To confirm that the phenotype we had observed with the $Ca_v2.2$ null hybrid mice was due to absence of the $Ca_v2.2$ gene, inbred 129/SvJae $Ca_v2.2$ null and wild-type mice were studied since these mice are genetically identical except for the $Ca_v2.2$ allele. A measure of ethanol reward: conditioned place preference, and a measure of acute response: loss of the righting reflex, were assessed. Inbred 129/SvJae mice showed the same phenotype as their F1 hybrid counterparts; $Ca_v2.2$ null showed no conditioned place preference for ethanol, and decreased duration of the ethanol-induced LORR compared with wild-type littermates (FIG. 7).

Discussion of Examples

The foregoing examples demonstrate for the first time that N-type calcium channels modulate behavioral responses to acute and chronic ethanol exposure. Particularly important are the findings that $Ca_v2.2$ null mice consume about 30% less alcohol than wild-type littermates when provided solutions containing 6% or 10% ethanol and show no ethanol-induced place preference at any dose of ethanol tested. These findings indicate that ethanol reward requires N-type calcium channels and indicate that N-type channel inhibitors will reduce ethanol consumption.

Although $Ca_v2.2$ null mice developed conditioned taste aversion to ethanol, it was significantly reduced in magnitude when compared to wild-type mice, indicating that the aversive effects of ethanol are also reduced in $Ca_v2.2$ null mice. Conditioned taste aversion, like conditioned place preference, is a classical conditioning phenomenon generated by the formation of an association between a conditioned stimulus (CS, 1.2% NaCl) and an unconditioned stimulus (US, 2 g/kg ethanol injection) (Welzl et al., 2001). Thus, the ability of $Ca_v2.2$ null mice to develop significant conditioned taste aversion demonstrates they are capable of learning by a simple CS-US association, confirming that the conditioned place preference results were not due to a learning defect.

In addition to impaired ethanol reward and consumption, and reduced aversion, $Ca_v2.2$ null mice also showed a 70% decrease in the duration of the ethanol induced LORR and a 16% increase in the threshold ethanol dose that induces LORR when compared with wild-type mice. Acute ethanol exposure inhibits the function of N-type calcium channels (Solem et al., 1997). This finding, together with the results of our current study, suggest that inhibition of N-type calcium channels contributes to the hypnotic effects of ethanol and that absence of N-type channels limits this behavioral response. The much greater effect of gene deletion on LORR duration compared with LORR threshold dose suggests that N-type channels contribute not only to initial sensitivity but also to acute tolerance to the hypnotic effect of ethanol.

Ethanol-induced LORR assesses the response to high anesthetic doses of ethanol. To examine the response to a lower intoxicating dose, ethanol-induced ataxia was measured. Interestingly, $Ca_v2.2$ null mice displayed an increase in sensitivity to ethanol-induced ataxia. This response was modest, present only when mice were tested on an accelerating rotarod, but not on a fixed-rate apparatus. This suggests that N-type channels play a minor role in moderating the effects of ethanol on coordination. The findings of increased ethanol-induced ataxia and diminished ethanol-induced LORR indicate that the ethanol phenotype of $Ca_v2.2$ null mice is not simply due to a global, unidirectional, change in acute sensitivity, but is behavior-specific.

Many different knockout and transgenic mouse lines have been screened for altered responses to ethanol. The prevailing pattern in these studies is an inverse correlation between changes in sensitivity to the acute intoxicating properties of ethanol, generally assayed by loss of the righting reflex, and changes in voluntary ethanol consumption (Thiele et al., 1998; Hodge et al., 1999; Thiele et al., 2000; Weinshenker et al., 2000; Wand et al., 2001; Naassila et al., 2002; Spanagel et al., 2002; Thiele et al., 2002; Naassila et al., 2004). This relationship fits well with observations in some human subjects, where low response to an alcohol challenge correlates with increased likelihood of future alcohol abuse or dependence (Schuckit, 1994). According to this pattern, the decreased acute sensitivity shown by $Ca_v2.2$ null mice would predict increased voluntary ethanol consumption, but instead the amount of ethanol consumed by these mice was significantly reduced compared to wild-type animals. This striking combination of results may be explained by the presence of ethanol conditioned taste aversion but the complete absence of ethanol conditioned place preference in these animals, suggesting that $Ca_v2.2$ null mice do not drink ethanol because they experience its aversive effects, but do not find it rewarding.

N-type calcium channels regulate the release of neurotransmitters and neuropeptides known to be important for mediating behavioral responses to alcohol, such as glutamate (Krystal et al., 2003), GABA (Davies, 2003), and endogenous opioids (Oswald and Wand, 2004). For example, ethanol stimulates release of beta-endorphin from primary cultures of hypothalamic neurons and this is prevented by pre-treatment with the N-type calcium channel antagonist omega-conotoxin GVIA (De Boyadjieva and Sarkar, 1999). N-type calcium channels regulate release of glutamate (Gruner and Silva, 1994), whose actions at NMDA receptors are inhibited by ethanol (Allgaier, 1002). N-type calcium channels can also modulate the release of GABA (Momiyama, 2001) and interactions between ethanol and GABA at GABAA receptors contribute to acute behavioral effects of alcohol (Davies, 2003). In addition. N-type calcium channels are a site of action for several neuromodulators known to play significant roles in ethanol reward, such as opioids (Kitamura et al., 2002; Hjelmstad and Fields, 2003), cannabinoids (Twitchell et al., 1997) and dopamine (Momiyama and Koga, 2001). Consistent with the importance of these modulators in ethanol self-administration is the finding that mice deficient in CB 1 canna-binoid receptors (Naassila et al., 2004), μ-opioid receptors (Roberts et al., 2000), or D2 dopamine receptors (Phillips et al., 1998) consume less alcohol than wild type littermates.

References

Allgaier C. (2002) Ethanol sensitivity of NMDA receptors. Neurochem Int 41:377-382.

Bernard C., Corzo G., Mosbah A., Nakajima T. and Darbon H. (2001) Solution structure of Ptu1, a toxin from the assassin bug Peirates turpis that blocks the voltage-sensitive calcium channel N-type. Biochemistry 40:12795-1280.

Beuckmann C T, Sinton C M, Miyamoto N, Ino M, Yanagisawa M (2003) N-type calcium channel alpha1B subunit ($Ca_v2.2$) knock-out mice display hyperactivity and vigilance state differences. J Neurosci 23:6793-6797.

Bowers B J, Owen E H, Collins A C, Abeliovich A, Tonegawa S, Wehner JM (1999) Decreased ethanol sensitivity and tolerance development in gamma-protein kinase C null mutant mice is dependent on genetic background. Alcoholism, Clinical and Experimental Research 23:387-397.

Brooks S P, Hennebry G, McAlpin G P, Norman G, Little H J (2002) Nimodipine prevents the effects of ethanol in tests of memory. Neuropharmacology 42:577-585.

Brown L M, Sims J S, Randall P, Wilcox R, Leslie S W (1993) ω-conotoxin increases sleep time following ethanol injection. Alcohol 10: 159-162.

Chester J A, Lumeng L, Li T K, Grahame N J (2003) High- and low-alcohol-preferring mice show differences in conditioned taste aversion to alcohol. Alcohol Clin Exp Res 27:12-18.

Cunningham C L, Henderson C M (2000) Ethanol-induced conditioned place aversion in mice. Behav Pharmacol 11:591-602.

Davies M. (2003) The role of GABAA receptors in mediating the effects of alcohol in the central nervous system. J Psychiatry Neurosci 28:263-274.

De A, Boyadjieva N I, Sarkar D K (1999) Effect of voltage-dependent calcium channel blockers on ethanol-induced beta-endorphin release from hypothalamic neurons in primary cultures. Alcohol Clin Exp Res 23:850-855.

De Beun R, Schneider R, Klein A, Lohmann A, De Vry J (1996) Effects of nimodipine and other calcium channel antagonists in alcohol-preferring AA rats. Alcohol 13:263-271.

Dickinson S D, Lee E L, Rindal K, Cunningham C L (2003) Lack of effect of dopamine receptor blockade on expression of ethanol-induced conditioned place preference in mice. Psychopharmacology (Berl) 165:238-244.

Dixon W (1965) The Up-and-Down Method for Small Samples. J Am Stat Assoc 60:967-978.

Dudek B C, Phillips T J (1990) Distinctions among sedative, disinhibitory, and ataxic properties of ethanol in inbred and selectively bred mice. Psychopharmacology (Berl) 101:93-99.

Dunlap K, Luebke J I, Turner T J (1995) Exocytotic Ca2+ channels in mammalian central neurons. Trends in Neurosciences 18:89-98.

Fadda F, Garau B, Colombo G, Gessa G L (1992) Isradipine and other calcium channel antagonists attenuate ethanol consumption in ethanol-preferring rats. Alcoholism: Clinical and Experimental Research 16:449-452.

Favreau P., Gille s N., Lamthanh H., Bournaud R., Shimahara T., Bouet F., et al. (2001) A new omega-conotoxin that targets N-type voltage-sensitive calcium channels with unusual specificity. Biochemistry 40:14567-14575.

Findlay G S, Wick M J, Mascia M P, Wallace D, Miller G W, Harris R A, Blednov Y A (2002) Transgenic expression of a mutant glycine receptor decreases alcohol sensitivity of mice. J Pharmacol Exp Ther 300:526-534.

Ghosh A, Greenberg M E (1995) Calcium signaling in neurons: Molecular mechanisms and cellular consequences. Science 268:239-247.

Gruner W. and Silva L. R. (1994) Omega-conotoxin sensitivity and presynaptic inhibition of glutamatergic sensory neurotransmission in vitro. J Neurosci 14:2800-2808.

Hjelmstad G. O. and Fields H. L. (2003) Kappa opioid receptor activation in the nucleus accumbens inhibits glutamate and GABA release through different mechanisms. J Neurophysiol 89:2389-2395.

Hodge C W, Mehmert K K, Kelley S P, McMahon T, Haywood A, Olive M F, Wang D, Sanchez-Perez A M, Messing R O (1999) Supersensitivity to allosteric GABAA receptor modulators and alcohol in mice lacking PKC□. Nature Neuroscience 2:997-1002.

Kim C, Jun K, Lee T, Kim S S, McEnery M W, Chin H, Kim H L, Park J M, Kim D K, Jung S J, Kim J, Shin H S (2001) Altered nociceptive response in mice deficient in the alpha(1B) subunit of the voltage-dependent calcium channel. Mol Cell Neurosci 18:235-245.

Kitamura G., Ohta T., Kai T., Kon Y. and Ito S. (2002) Inhibitory effects of opioids on voltage-dependent Ca(2+) channels and catecholamine secretion in cultured porcine adrenal chromaffin cells. Brain Res 942:11-22.

Krystal J. H., Petrakis I. L., Mason G., Trevisan L. and D'Souza D. C. (2003) N-methyl-D-aspartate glutamate receptors and alcoholism: reward, dependence, treatment, and vulnerability. Pharmacol Ther 99:79-94.

Kuzmin A, Semenova S, Zvartau E, De Vry J (1999) Effects of calcium channel blockade on intravenous self-administration of ethanol in rats. Eur Neuropsychopharmacol 9:197-203.

Lewis R. J., Nielsen K. J., Craik D. J., Loughnan M. L., Adams D. A., Sharpe I. A., et al. (2000) Novel omega-conotoxins from Conus catus discriminate among neuronal calcium channel subtypes. J Biol Chem 275:35335-35344.

Little H J (1995) The role of calcium channels in drug dependence. Drug Alcohol Depend 38:173-194.

McMahon T, Andersen R, Metten P, Crabbe J C, Messing R O (2000) Protein kinase C epsilon mediates up-regulation of N-type calcium channels by ethanol. Molecular Pharmacology 57:53-58.

Momiyama T. and Koga E. (2001) Dopamine D(2)-like receptors selectively block N-type Ca(2+) channels to reduce GABA release onto rat striatal cholinergic interneurones. J Physiol 533:479-492.

Naassila M, Ledent C, Daoust M (2002) Low ethanol sensitivity and increased ethanol consumption in mice lacking adenosine A2A receptors. J Neurosci 22:10487-10493.

Naassila M, Pierrefiche 0, Ledent C, Daoust M (2004) Decreased alcohol self-administration and increased alcohol sensitivity and withdrawal in CB 1 receptor knockout mice. Neuropharmacology 46:243-253.

Olive M F, Koenig H N, Nannini M A, Hodge C W (2001) Stimulation of endorphin neurotransmission in the nucleus accumbens by ethanol, cocaine, and amphetamine. J Neurosci 21:RC184.

Olivera B M, Miljanich G P, Ramachandran J, Adams M E (1994) Calcium channel diversity and neurotransmitter release: The ω-conotoxins and ω-agatoxins. Annual Review of Biochemistry 63:823-867.

Oswald L. M. and Wand G. S. (2004) Opioids and alcoholism. Physiol Behav 81:339-358.

Phillips T. J., Brown K. J., Burkhart-Kasch S., Wenger C. D., Kelly M. A., Rubinstein M., et al. (1998) Alcohol preference and sensitivity are markedly reduced in mice lacking dopamine D2 receptors. Nat Neurosci 1:610-615.

Pucilowski O, Ayensu W K, D'Ercole A J (1996) Insulin-like growth factor I expression alters acute sensitivity and tolerance to ethanol in transgenic mice. Eur J Pharmacol 305:57-62.

Rezvani A H, Janowsky D S (1990) Decreased alcohol consumption by verapamil in alcohol preferring rats. Progress in Neuro-Psychopharmacology and Biological Psychiatry 14:623-631.

Rezvani A H, Grady D R, Janowsky D S (1991) Effect of calcium-channel blockers on alcohol consumption in alcohol-drinking monkeys. Alcohol & Alcoholism 26:161-167.

Risinger F O, Boyce J M (2002) Conditioning tastant and the acquisition of conditioned taste avoidance to drugs of abuse in DBA/2J mice. Psychopharmacology (Berl) 160: 225-232.

Risinger F O, Freeman P A, Greengard P, Fienberg A A (2001) Motivational effects of ethanol in DARPP-32 knock-out mice. J Neurosci 21:340-348.

Roberts A. J., McDonald J. S., Heyser C. J., Kieffer B. L., Matthes H. W., Koob G. F., et al. (2000) mu-Opioid receptor knockout mice do not self-administer alcohol. J Pharmacol Exp Ther 293:1002-1008.

Rusin K I, Moises H C (1995) µ-opioid receptor activation reduces multiple components of high-threshold calcium current in rat sensory neurons. Journal of Neuroscience 15:4315-4327.

Schuckit M A (1994) Low level of response to alcohol as a predictor of future alcoholism. American Journal of Psychiatry 151:184-189.

Soldo B L, Moises H C (1997) µ-opioid receptor activation decreases N-type Ca2+ current in magnocellular neurons of the rat basal forebrain. Brain Research 758:118-126.

Solem M, McMahon T, Messing R O (1997) Protein kinase A regulates inhibition of N- and P/Q-type calcium channels by ethanol in PC12 cells. Journal of Pharmacology and Experimental Therapeutics 282:1487-1495.

Spanagel R, Siegmund S, Cowen M, Schroff K C, Schumann G, Fiserova M, Sillaber I, Wellek S, Singer M, Putzke J (2002) The neuronal nitric oxide synthase gene is critically involved in neurobehavioral effects of alcohol. J Neurosci 22:8676-8683.

Suh H W, Song D K, Choi S R, Huh S O, Kim Y H (1997) Differential effects of omega-conotoxin GVIA, nimodipine, calmidazolium and KN-62 injected intrathecally on the antinociception induced by beta-endorphin, morphine and [D-Ala2,N-MePhe4,Gly-ol5]-enkephalin administered intracerebroventricularly in the mouse. J Pharmacol Exp Ther 282:961-966.

Thiele T E, Koh M T, Pedrazzini T (2002) Voluntary alcohol consumption is controlled via the neuropeptide Y Y1 receptor. J Neurosci 22:RC208.

Thiele T E, Marsh D J, Ste. Marie L, Bernstein I L, Palmiter R D (1998) Ethanol consumption and resistance are inversely related to neuropeptide Y levels. Nature 396: 366-369.

Thiele T E, Willis B, Stadler J, Reynolds J G, Bernstein I L, McKnight G S (2000) High ethanol consupmtion and low sensitivity to ethanol-induced sedation in protein kinase A-mutant mice. Journal of Neuroscience 20:RC75.

Twitchell W., Brown S. and Mackie K. (1997) Cannabinoids inhibit N- and P/Q-type calcium channels in cultured rat hippocampal neurons. J Neurophysiol 78:43-50.

Tzschentke T M (1998) Measuring reward with the conditioned place preference paradigm: a comprehensive review of drug effects, recent progress and new issues. Prog Neurobiol 56:613-672.

Ulm R R, Volpicelli J R, Volpicelli L A (1995) Opiates and alcohol self-administration in animals. J Clin Psychiatry 56 Suppl 7:5-14.

Walter H, Messing R O (1999) Regulation of neuronal voltage-gated calcium channels by ethanol. Neurochemistry International 35:95-101.

Wand G, Levine M, Zweifel L, Schwindinger W, Abel T (2001) The cAMP-protein kinase A signal transduction pathway modulates ethanol consumption and sedative effects of ethanol. Journal of Neuroscience 21:5297-5303.

Wang X, Lemos J R, Dayanithi G, Nordmann J J, Treistman S N (1991) Ethanol reduces vasopressin release by inhibiting calcium currents in nerve terminals. Brain Research 551:339-341.

Watson W P, Little H J (1999) Correlation between increases in dihydropyridine binding in vivo and behavioural signs of ethanol withdrawal in mice. Alcohol Alcohol 34:35-42.

Weinshenker D, Rust N C, Miller N S, Palmiter R D (2000) Ethanol-associated behaviors of mice lacking norepinephrine. Journal of Neuroscience 20:3157-3164.

Welzl H, D'Adamo P, Lipp H P (2001) Conditioned taste aversion as a learning and memory paradigm. Behav Brain Res 125:205-213.

Zamponi G W, Bourinet E, Nelson D, Nargeot J, Snutch T P (1997) Crosstalk between G proteins and protein kinase C mediated by the calcium channel α1 subunit. Nature 385:442-446.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing an ethanol-related effect or behavior, the method comprising administering an N-type calcium channel inhibitor to a subject in need of reduction of the ethanol-related effect or behavior, whereby the ethanol-related effect or behavior is reduced, and wherein the ethanol-related effect or behavior comprises an effect or behavior selected from the group consisting of a sedative effect, a hypnotic effect, drug reward, and drug consumption.

2. The method of claim 1, wherein the N-type calcium channel inhibitor is selected from the group consisting of omega conotoxin MVIIC, omega grammotoxin SIA, and omega agatoxin IIIA.

3. The method of claim 1, wherein the N-type calcium channel inhibitor is a selective N-type calcium channel inhibitor.

4. The method of claim 3, wherein the N-type calcium channel inhibitor is selected from the group consisting of omega-conotoxin MVIIA, and NMED-160.

5. The method of claim 1, wherein the N-type calcium channel inhibitor inhibits a function of N-type calcium channels.

6. The method of claim 5, wherein the N-type calcium channel inhibitor inhibits phosphorylation of N-type calcium channels.

7. The method of claim 5, wherein the N-type calcium channel inhibitor enhances the interaction between N-type calcium channels and β-γ subunits of a G protein.

8. The method of claim 1, wherein the N-type calcium channel inhibitor educes the level of N-type calcium channels in a tissue.

9. The method of claim 8, wherein the N-type calcium channel nhibitor reduces the level of N-type $Ca_v2.2$ subunits in the tissue.

10. The method of claim 1, wherein the ethanol-related effect or behavior comprises a sedative effect.

11. The method of claim 1, wherein the ethanol-related effect or behavior comprises a hypnotic effect.

12. The method of claim 1, wherein the ethanol-related effect or behavior comprises drug reward.

13. The method of claim 1, wherein the ethanol-related effect or behavior comprises drug consumption.

14. The method of claim 1, wherein the subject is a human.

* * * * *